US006784342B1

(12) United States Patent
Kunst et al.

(10) Patent No.: US 6,784,342 B1
(45) Date of Patent: Aug. 31, 2004

(54) REGULATION OF EMBRYONIC TRANSCRIPTION IN PLANTS

(75) Inventors: Ljerka Kunst, North Vancouver (CA); Sabine Clemens, Vancouver (CA)

(73) Assignee: The University of British Columbia, Vancouver (CA)

(*) Notice: Subject to any disclaimer, the term of this patent is extended or adjusted under 35 U.S.C. 154(b) by 0 days.

(21) Appl. No.: 09/806,708

(22) PCT Filed: Aug. 4, 2000

(86) PCT No.: PCT/CA00/00907

§ 371 (c)(1),
(2), (4) Date: Apr. 3, 2001

(87) PCT Pub. No.: WO01/11061

PCT Pub. Date: Feb. 15, 2001

Related U.S. Application Data

(60) Provisional application No. 60/147,133, filed on Aug. 4, 1999.

(51) Int. Cl.$^7$ .......................... C12N 15/82; A01H 5/00; A01H 1/00

(52) U.S. Cl. ...................... 800/298; 800/278; 800/287; 800/281; 536/24.1; 435/468; 435/419; 435/320.1

(58) Field of Search ............................... 800/278, 287, 800/298, 281, 290; 536/24.1, 23.6, 23.1; 435/468, 419, 320.1

(56) References Cited

U.S. PATENT DOCUMENTS

| | | | |
|---|---|---|---|
| 5,623,067 A | 4/1997 | Vandekerckhove et al. | |
| 5,792,922 A | 8/1998 | Maloney | |

FOREIGN PATENT DOCUMENTS

| | | |
|---|---|---|
| WO | WO 9515387 | 6/1995 |
| WO | WO 9613582 | 5/1996 |
| WO | WO 98/45461 | 10/1998 |
| WO | WO 9846766 | 10/1998 |
| WO | WO 9854954 | 12/1998 |
| WO | WO 9903983 | 1/1999 |
| WO | WO 9954471 | 10/1999 |

OTHER PUBLICATIONS

Sindhu et al., The pea seed storge protein legumin was synthesized, processed, and accumlated stably in transgenic rice endosperm, 1997. Plant Science, vol. 130, pp. 189–196.*
Lohmann et al., A Molecular Link between Stem Cell Regulation and Floral Patterning in Arabidipsis. Jun. 15, 2001, Cell, vol. 105, pp. 793–803.*
Busch et al., Activation of a Floral Homeotic Gene in Arabidopsis. Jul. 23, 1999. Science vol. 285, pp. 585–587.*
Izawa et al., Plant bZIP Protein DNA Binding Specificity, 1993. J Mol. Biol., vol. 230, pp. 1131–1144.*
Hao et al., Unique Mode of GCC Box Recognition by the DNA–binding Domain of . . . Oct. 9, 1998, The Journal of Biological Chemistry, vol. 273, No. 41, pp. 26857–26861.*
Eshed et al., Establisment of polarity in lateral organs of plants. 2001, Current Biology, vol. 11, pp. 1251–1260.*
Finnegan et al., Transgene Inactivation: Plant Fight Back!, Sep. 1994. Bio/Technology, vol. 12, pp. 883–887.*
Benfey et al., "Regulated genes in transgenic plants," *Science* 244:174–181, 1989.
Beyan et al., "Tissue– and cell–specific activity of a phenylalanine ammonia–lyase promoter in transgenic plants," *EMBO J.* 8:1899–1906, 1989.
Katavic et al., "*In planta* transformation of *Arabidopsis thaliana*," *Mol. Gen. Genet.* 245:363–370, 1994.
Konez et al., "The promoter of $T_L$–DNA gene 5 controls the tissue–specific expression of chimaeric genes carried by a novel type of *Agrobacterium* binary vector," *Mol. Gen. Genet.* 204:383–396, 1986.
Lee et al., "Manipulation of plant gene expression using antisense RNA," In: *Plant Biochemistry/Molecular Laboratory Manual* pp. 423–439, Dashek, WV. ed., CRC Press. Inc. Boca Raton, 1996.
Murphy et al., "Immunocytochemical and biochemical study of the biosynthesis and mobilisation of the major seed storage proteins of *Brassica napus*, " *Plant. Physiol. Biochem.* 27:647–657, 1989.
Stalberg et al., "Disruption of an overlapping E–box–ABRE motif abolished high transcription of the napA storage–protein promoter in transgenic *Brassica napus* seed, " *Plant* 199:515–519, 1996.
Voelker et al., "Genetic engineering of a quantitative trait: metabolic and genetic parameters influencing the accumulation of laurate in rapeseed," *Plant J.* 9:229–241, 1996.
Rowley et al., "The upstream domain of soybean olesin genes contains regulatory elements similar to those of legume storage proteins, " *Biochim. Biophys. Acta* 1345:1–4, 1997.
Morton et al., "Regulation of Seed Storage Protein Gene Expression," Kigel and Gallili, eds., pp. 103–138, Marcel Dekker, New York, 1994.
Kawagoe et al., "Four distinct nuclear proteins recognize in vitro proximal promoter of the bean seed storage protein β–phaseolin gene conferring spatial and temporal control," *Plant J.* 2:927–936, 1992.

(List continued on next page.)

*Primary Examiner*—Elizabeth F. McElwain
*Assistant Examiner*—Stuart F. Baum
(74) *Attorney, Agent, or Firm*—Klarquist Sparkman LLP

(57) ABSTRACT

Nucleic acid constructs are provided comprising transcriptional regulatory regions homologous to plant FAE1 promoters. In some embodiments, these constructs may be used in transgenic cells or plants to promote expression of foreign and endogenous genes in developing seeds, for example to affect seed lipid metabolism, protein or carbohydrate composition and accumulation, or seed development.

10 Claims, 15 Drawing Sheets

OTHER PUBLICATIONS

Shen et al., "Functional Dissection of an Abscisc Acid (ABA)—Inducible Gene *Reveals Two Independent ABA— Responsive Complexes Each Containing a G–Box* and a Novel cis–Acting Element," *Plant Cell* 7:295–307, 1995.

Dickinson et al., "RY repeats are conserved in the 5'-flakning regions of legume seed–protein genes," *Nucleic Acid Res.*, 16:371, 1988.

Lelievre et al., "5'–CATGCAT–3'Elements Modulate the Expression of Glycinin Genes" *Plant Physiol.* 98:387–391, 1992.

Chen et al., "A DNA sequence element that confers seed– specific enhancement to a constitutive promoter," *EMBO J.* 7:297–302, 1988.

Shen et al., "Modular Nature of Abscisic Acid (ABA) Response Complexes: Composite Promoter Units That Are Neccessary and Sufficient for ABA Induction of Gene Expression in Barley," *Plant Cell* 8:1107–1119, 1996.

James et al., "Directed Tagging of the Arabidopsis *Fatty Acid Elongation* (*FAE1*) Gene with the Maize Transposon Activator," *Plant Cell* 7:309–319, Mar. 1995.

Kunst et al., "Fatty acid elongatio in developing seeds of *Arabidopsis thaliana*," *Plant Physiol. Biochem.* 30(2):425–434, 1992.

Millar et al., "*CUT1*, an Arabidopsis Gene Required for Cuticular Wax Biosynthesis and Pollen Fertility, Encodes a Very–Long–Chain Fatty Acid Condensing Enzyme," *Plant Cell* 11:825–838, May 1999.

Clemens and Kunst, Accession No. AF009563, Jul. 24, 1997.

James et al., Accession No. U29142, Jul. 4, 1995.

Roscoe et al., Accession No. U50771, Apr. 6, 1996.

Venkateswari et al., "Molecular Cloning and Characterization of *Fatty Acid Elongation* (*BjFAE1*) *gene of Brassica juncea*," *J. Plant Biochem. Biotech.* 8(1):53–55, Jan. 1999.

* cited by examiner

ARABIDOPSIS THALIANA FAE1 PROMOTER:
(LENGTH 934 bp)

```
-950       ACTCA TAAAAACTAG TAGATTGGTT GGTTGGTTTC CATGTACCAG
                             AtproFW →
-900 AAGGCTTACC CTATTAGTTG AAAGTTGAAA CTTTGTTCCC TACTCAATTC
-850 CTAGTTGTGT AAATGTATGT ATATGTAATG CGTATAAAAC GTAGTACTTA
-800 AATGACTAGG AGTGGTTCTT GAGACCGATG AGAGATGGGA GCAGAACTAA
-750 AGATGATGAC ATAATTAAGA ACGAATTTGA AAGGCTCTTA GGTTTGAATC
-700 CTATTCGAGA ATGTTTTGT CAAAGATAGT GGCGATTTTG AACCAAAGAA
-650 AACATTTAAA AAATCAGTAT CCGGTTACGT TCATGCAAAT AGAAAGTGGT
-600 CTAGGATCTG ATTGTAATTT TAGACTTAAA GAGTCTCTTA AGATTCAATC
-550 CTGGCTGTGT ACAAAACTAC AAATAATATA TTTTAGACTA TTTGGCCTTA
-500 ACTAAACTTC CACTCATTAT TTACTGAGGT TAGAGAATAG ACTTGCGAAT
-450 AAACACATTC CCGAGAAATA CTCATGATCC CATAATTAGT CAGAGGGTAT
-400 GCCAATCAGA TCTAAGAACA CACATTCCCT CAAATTTTAA TGCACATGTA
-350 ATCATAGTTT AGCACAATTC AAAAATAATG TAGTATTAAA GACAGAAATT
-300 TGTAGACTTT TTTTTGGCGT TAAAGGAAGA CTAAGTTTAT ACGTACATTT
-250 TATTTTAAGT GGAAAACCGA AATTTTCCAT CGAAATATAT GAATTTAGTA
-200 TATATATTTC TGCAATGTAC TATTTTGCTA TTTTGGCAAC TTTCAGTGGA
-150 CTACTACTTT ATTACAATGT GTATGGATGC ATGAGTTTGA GTATACACAT
-100 GTCTAAATGC ATGCTTTGCA AAACGTAACG GACCACAAAA GAGGATCCAT
 -50 GCAAATACAT CTCATAGCTT CCTCCATTAT TTCCGACAC AAACAGAGCA
                                     ← AtproRV
   1 ATGACGTCCG TTAACGTTAA GCTCCTT
```

FIG. 1

BRASSICA NAPUS FAE1 PROMOTER:
(LENGTH 1588 bp)

```
-1600 GGTTGGGCAA ATCTGACTTC ACCAAAGAAA CAACTCGAGT CGTTATCCAT
                   BnproFW →
-1550 CTCCTCATAA CCATCGCTCC ACTCTTTGCC TTCACCGTTT TCGGTTCGGT
-1500 TCTCTACATC GCAACCCGGC CCAAACCGGT TTACCTCGTT GAGTACTCAT
-1450 GCTACCTTCC ACCAACGCAT TGTAGATCAA GTATCTCCAA GGTCATGGAT
-1400 ATCTTTTATC AAGTAAGAAA AGCTGATCCT TCTCGGAACG GCACGTGCGA
-1350 TGACTCGTCG TGGCTTGACT TCTTGAGGAA GATTCAAGAA CGTTCAGGTC
-1300 TAGGCGATGA AACTCACGGG CCCGAGGGGC TGCTTCAGGT CCCTCCCCGG
-1250 AAGACTTTTG CGGCGGCGCG TGAAGAGACG GAGCAAGTTA TCATTGGTGC
-1200 GCTAGAAAAT CTATTCAAGA ACACCAACGT TAACCCTAAA GATATAGGTA
-1150 TACTTGTGGT GAACTCAAGC ATGTTTAATC CAACTCCATC GCTCTCCGCG
-1100 ATGGTCGTTA ACACTTTCAA GCTCCGAAGC AACGTAAGAA GCTTTAACCT
-1050 TGGTGGCATG GGTTGTAGTG CCGGCGTTAT AGCCATTGAT CTAGCAAAGG
-1000 ACTTGTTGCA TGTCCATAAA AATACGTATG CTCTTGTGGT GAGCACAGAG
 -950 AACATCACTT ATAACATTTA CGCTGGTGAT AATAGGTCCA TGATGGTTTC
 -900 AAATTGCTTG TTCCGTGTTG GTGGGCCGC TATTTGCTC TCCAACAAGC
 -850 CTGGAGATCG TAGACGGTCC AAGTACGAGC TAGTTCACAC GGTTCGAACG
 -800 CATACCGGAG CTGACGACAA GTCTTTTCGT TGCGTGCAAC AAGGAGACGA
 -750 TGAGAACGGC AAAATCGGAG TGAGTTTGTC CAAGGACATA ACCGATGTTG
 -700 CTGGTCGAAC GGTTAAGAAA AACATAGCAA CGTTGGGTCC GTTGATTCTT
 -650 CCGTTAAGCG AGAAACTTCT TTTTTTCGTT ACCTTCATGG GCAAGAAACT
 -600 TTTCAAAGAT AAAATCAAAC ATTACTACGT CCCGGATTTC AAACTTGCTA
 -550 TTGACCATTT TTGTATACAT GCCGGAGGCA GAGCCGTGAT TGATGTGCTA
 -500 GAGAAGAACC TAGCCCTAGC ACCGATCGAT GTAGAGGCAT CAAGATCAAC
```

FIG. 2A

BRASSICA NAPUS FAE1 PROMOTER:
(CONTINUED)

```
-450 GTTACATAGA TTTGGAAACA CTTCATCTAG CTCAATATGG TATGAGTTGG

-400 CATACATAGA AGCAAAAGGA AGGATGAAGA AAGGTAATAA AGTTTGGCAG

-350 ATTGCTTTAG GGTCAGGCTT TAAGTGTAAC AGTGCAGTTT GGGTGGCTCT

-300 AAACAATGTC AAAGCTTCGA CAAATAGTCC TTGGGAACAC TGCATCGACA

-250 GATACCCGGT CAAAATTGAT TCTGATTCAG GTAAGTCAGA GACTCGTGTC

-200 CAAAACGGTC GGTCCTAATA AACGATGTTT GCTCTCTTTC GTTTCTTTTT

-150 ATTTGTTATA ATAATTTGAT GGCTACGATG TTTCTCTTGT TTGTTATGAA

-100 TAAAGAATGC AATGGTGTTC TAGTATTTGA TTGTTTTACA TGTATGTATC

-50 TCTTATTTAC ATGAAATTTT TAAACGCCTA AAAAAAAAAA CGGAATTCCG
                                        ← BnproRV
   1 ATG ACGTCCA TTAACGTAAA GCTCCTTTAC CATTACGTCA TAACCAACCT 51 TTTCAACCTT TGCTTCTTTC CGTTAACGGC GATCGTCGCC GGAAAAGCCT
        ← Bnwalk2
 101 ATCGGCTTAC CATAGACGAT CTTCACCACT TATACTATTC CTATCTCCAA 151 CACAACCTCA TAACCATCGC TCCACTCTTT GCCTTCACCG
               ← Bnwalk1
```

FIG. 2B

LUNARIA ANNUA FAE1 PROMOTER:
(LENGTH 1069 bp)

```
-1100                     CG CCGGGGAGTT TCAGCTTAAC CGGTAAAATT
                                                  LproFW →
-1050 GGCCTGTACA TATATTTACC ACTGAGTAAA GACATCAGTT AATGATTTGT
-1000 TGTTACTCAA TTGGGCTAAG TGTATTATTA TATGTGTTGT ATATAATAAA
 -950 GGTAGAACGT AAATTTACTA AGAATGTGTT TTTCCAATGT GATTGCTCTT
 -900 TGGCCTCTTA GGTTTGAATC CTACTCGAGA AGACTAATTT TAATTTACTG
 -850 GCAAAAATAG AAATCAATTT ATAAGTGTTT AAACAAATCG ATGGTATAAC
 -800 TGATTAGTGA TCACTCTTAG GTTTTGATCC AACTCGAGTA TTGAGTATTG
 -750 AACGCTTTTT TTAAATAAAA TCTTGATTTT TAAATTGGTT TTTTGAGTAA
 -700 AAAAGTTCTT AATATTTTCT CTTTGTTTTA ATGGGTTTGT TTTGCATTTT
 -650 ATAAGCTTAA TTTTTCTAAT TTAATATTTT ATCTATCATC GTCCGTAAAG
 -600 TTTTATTTGG CACAAACTTG TTTTACTTTT CTACCTTATA ATTTGGGAAC
 -550 TGGTTGAGTC AAAGCGTACC GGACAAATAT GTTTTATATT CTTATTTAAG
 -500 AATTAACACT CATCTCATAA TTAGTCAGAG GCTAGGGAGA TTCAGCCAAT
 -450 CAATGCTAAC AACAAAATTC TCTTAATGAT CTAACGATGC TATTTAATAT
 -400 TCGGATCAGT ATTCTTAAAT AAGAATATAA AACTAATTCA ATAGTTACAG
 -350 ATAAAAACTT ATATAGACTT TTTTATTTGG AATATAAAAG TATCAATATA
 -300 TTATAGACAA TATTTATAAC GTTAAAAATA CAATATTTAT ATTTTTTATA
 -250 TATTTATTTC AAATTGAAAA GCATTACTTC TATCGAAATG AATTTTAGTA
 -200 TATTAATTAA TATTTTTTA ATCGGACTAC TTTCCTATTT TGGCACCTTT
 -150 CATCTGACTA CTAATTTATT TCAATGTGTA TGCATGCATG AGCATGAGTA
```

FIG. 3A

**LUNARIA ANNUA FAE1 PROMOTER:
(CONTINUED)**

```
-100 ATACACATGT CTATATAAAT GCATGTAAAA CGTAACGGAC CACAAAAGTG

-50 GATCCATACA AATACATCTC ATCGCACCCT CTCCGACACA AAACTGAACA
                                             ← LaproRV
   1 ATGACGTCTG TGAACGTAAA ACTCCTTTAC CATTACGTCA TAACCAACTT 51 TTTCAACCTC TGTTTCTTCC CACTGACGGG GATCCTCGCC GGAAAAGGCT
               ← Lawalk2
 101 CTCGTCTTAC CACAAACGAT CTCCACCA
        ← Lawalk1
```

FIG. 3B

ALIGNMENT OF *A.t.*, *L.a.* AND *B.n.* FAE1 PROMOTERS
CLUSTAL W (1.74) MULTIPLE SEQUENCE ALIGNMENT

```
A.t.   ------------------------------------------------------------
L.a.   ------------------------------------------------------------
B.n.   GGTTGGGCAAATCTGACTTCACCAAAGAAACAACTCGAGTCGTTATCCATCTCCTCATAA

A.t.   ------------------------------------------------------------
L.a.   ------------------------------------------------------------
B.n.   CCATCGCTCCACTCTTTGCCTTCACCGTTTTCGGTTCGGTTCTCTACATCGCAACCCGGC

A.t.   ------------------------------------------------------------
L.a.   ------------------------------------------------------------
B.n.   CCAAACCGGTTTACCTCGTTGAGTACTCATGCTACCTTCCACCAACGCATTGTAGATCAA

A.t.   ------------------------------------------------------------
L.a.   ------------------------------------------------------------
B.n.   GTATCTCCAAGGTCATGGATATCTTTTATCAAGTAAGAAAAGCTGATCCTTTTCGGAACG

A.t.   ------------------------------------------------------------
L.a.   ------------------------------------------------------------
B.n.   GCACGTGCGATGACTCGTCGTGGCTTGACTTCTTGAGGAAGATTCAAGAACGTTCAGGTC

A.t.   ------------------------------------------------------------
L.a.   ------------------------------------------------------------
B.n.   TAGGCGATGAAACTCACGGGCCCGAGGGGCTGCTTCAGGTCCCTCCCCGGAAGACTTTTG

A.t.   ------------------------------------------------------------
L.a.   ------------------------------------------------------------
B.n.   CGGCGGCGCGTGAAGAGACGGAGCAAGTTATCATTGGTGCGCTAGAAAATCTATTCAAGA

A.t.   ------------------------------------------------------------
L.a.   ------------------------------------------------------------
B.n.   ACACCAACGTTAACCCTAAAGATATAGGTATACTTGTGGTGAACTCAAGCATGTTTAATC

A.t.   ------------------------------------------------------------
L.a.   -------------------------------------CGCCGGGGAGTTTCAGCTTAA
B.n.   CAACTCCATCGCTCTCCGCGATGGTCGTTAACACTTTCAAGCTCCGAAGCAACGTAAGAA
                                            * *  * **   *    **
Con. 4                                     NNNNNNNNNNNNNNNNNNNNNNN

A.t.   ----------------------------ACTCATAAAAACTAGTAGAT--TGGTTGG
L.a.   CCGGTAAAATTGGCCTGTACATATATTTACCACTGAGTAAAGACATCAGTTAATGATTTG
B.n.   GCTTTAACCTTGGTGGCATGGGTTGTAGTGCCGGCGTTATAGCCATTGATCTAGCAAAGG
          *  ***  ****           *   *    *       *     *   *
Con. 4 NNNNNNNNNNNNNNNNNNNNNNNNNNNNNNNNNNNNMSKSRKWTWARMYCKYRRWYNNKSRWWKG
```

FIG. 4A

ALIGNMENT OF A.t., L.a. AND B.n. FAE1 PROMOTERS (CONTINUED)

```
A.t.    TTGGTTTCCA--TGTACCAGAAGGCTTACCCTAT-TAGTTGAAAGTTGAAACTTTGTTCC
L.a.    TTGTTACTCAATTGGGCTAAGTGTATTATTATAT-GTGTTGTATATAATAAAGGTAGAAC
B.n.    ACTTGTTGCATGTCCATAAAAATACGTATGCTCTTGTGGTGAGCACAGAGAACATCACTT
          **  *       *    **   *  *  * **       *    *
Con.4   WYKKKWYBCANNNTSBRYHARRWKDMKTAYBMTMTNKWGKTGWRHRYWRWRAMBDTVDHHY

A.t.    CTACTCAATTCCTAGTTGTGTAAATGT---ATGTATATGTAAT---GCGTATAAAACGTA
L.a.    GTAA--ATTTACTAAGAATGTGTTTTTCCAATGTGATTGCTCTTTGGCCTCTTAGGTTTG
B.n.    ATAA-CATTTACGCTGGTGATAATAGGTCCATGATGGTTTCAAATTGCTTGTTCCGTGTT
          **  **  **           *    *  ***     *   *   **  *       *
Con.4   VTAMNNAWTTMCMMDKDDKRTRWWWKKNNNATGWDDDTKYHMWNNNGCBTVTWMVRYKTD

A.t.    GTACTTAAATGACTAGGAGTGGTTCTTGAGACCGATGAGAGATGGGAG-CAGAACTAAAG
L.a.    AATCCTACTCGAGAAG-ACTAATTTTAATTTACTGGCAAAAATAGAAA-TCAATTTATAA
B.n.    GGTGGGGC-CGCTATTTTGCTCTCCAACAAGCCTGGAGATCGTAGACGGTCCAAGTACGA
                  *              *     *           *  *    *      **
Con.4   RDWSBKRMNYGMBWWKNWSYDVTYYWWVWDDMCKRKVRRWVRTRGRMRNYMVAWBTAHRR

A.t.    AT--GATGACATAATTA------AGAACGAATTTGA-AAGG-CTCTTAGGTTTGAATCCT
L.a.    GT--GTTTAAACAAATCGATGGTATAACTGATTAGT-GATCACTCTTAGGTTTTGATCCA
B.n.    GCTAGTTCACACGGTTCGAACGCATACCGGAGCTGACGACAAGTCTTTTCGTTGCGTGCA
          *  *  *     *       *   *    *      *   * * *    **   *   *
Con.4   RYNNGWTBAMAYRRWTMNNNNNNNAKAMCKRAKYWGWNRABVNSTCTTWKSKTTKVRTSCW

A.t.    ATTCGAGAATGTTTTTGTCAAAGATAGTGGCGATTTTGAACCAAAGAAAACATTTAAA-A
L.a.    ACTCGAGTATTGAGTATTGAACGCTT-------TTTTTAAATAAAATCTTGATTTTTA-A
B.n.    A--CAAGGA-GACGATGAGAACGGCAA-----AATCGGAGTGAGTTTGTCCAAGGACATA
        *  **  **  **           **  *        *          *        *-*
Con.4   ANNCRAGDANKDHKWWKWSAAMGVYWNNNNNNNWTYKKARHBARWDWVWHSAWKKWHANA

A.t.    AATCAGTATCCGGTTAC----GTTCATGCAAATAGAAAGTGGTCTA---GGATCTGATT-
L.a.    ATTGGTTTTTTGAGTAAAAAAGTTCTTAATATTTTCTCTTTGTTTTAATGGGTTTGTTT-
B.n.    ACCGATGTTGCTGGTCGAACGGTTAAGAAAAACATAGCAACGTT-----GGGTCCGTTGA
        *         *  ** ***     *         *    **   *      **   *
Con.4   AHYSRKKWTSYKRKTMVNNNNGTTMWKRMWAWYWKMDMDWBGTYNNNNNGGRTYYGWTKN

A.t.    GTAATTTAGA--CTTAAAGAGTCTC--TTAAGATTCAATCCTGGCT-GTGTACAAAACT
L.a.    TGCATTTTATAAGCTTAATTTTTCTAATTTAATATTTTATCTATCATCGTCCGTAAAGTT
B.n.    TTCTTCCGTTAAGCGAGAAACTTCTT--TTTTTCGTTA--CCTTCATGGGCAAGAAACTT
             *  **       *         ***                *    *  *   *
Con.4   KKMWTYYKWKANNCKWRAWDHKTCTHNNTTWWKMKTYWNNCYWKSMTNGKSHRBAAAVYT

A.t.    ACAAATAATATA----TTTTAGACTATTTGGCCTTAACTAAACTTCCA-CTCATTATTTA
L.a.    TTATTTGGCACAAACTTGTTTTACTTTTCTACCTTA--TAATTTGGGAACTGGTTGAGT-
B.n.    TTCAAAGATAAAATCAAACATTACTACGTCCCGGATTTCAAACTTGCTATTGACCATTTT
          *    *  *      *  *  **        *       **        *    **
Con.4   WYMWWWRRYAHANNNNWDYWWKACTWYKYBVCSKWWNNYAAWYTKSSHNYTSRYYRWKTN

A.t.    -CTGAGGTTAGAGAA--TAGACTTGCGAATAAACACATTCCCGAGAAATACTCATGATCC
L.a.    -CAAAGCGTACCGGA--CAAATATGTTT-TATATTCTTATTTAAGAATTAACACTCATCT
B.n.    TGTATACATGCCGGAGGCAGAGCCGTGATTGATGTGCTAGAGAAGAACCTAGCCCTAGCA
             *  * *     * *     *    *    *   *     **     *    *
Con.4   NSWRWRSDTRSMGRANNYARABHYGYKWNTRWWBWSHTWBHBRAGAAHYWMBHMYBAKCH
```

FIG. 4B

ALIGNMENT OF *A.t., L.a.* AND *B.n. FAE1* PROMOTERS *(CONTINUED)*

```
                                                       CE3
A.t.    CATAATTAGTCAGAGGGTATG---------CCAATCAGATCTAAGAAC ACACATTCCCTC
L.a.    CATAATTAGTCAGAGGCTAGGGAGATTCAGCCAATCAATGCTAACAACAAA-ATTCTCTT
B.n.    CCGATCGATGTAGAGGC-----------------ATCAAGATCAACGTTACATAGATTTGG
         *   *   *    **** **   *          ******    **   *  *

Con.4   CMKAWYKAKKYAGAGGSNNNNNNNNNNNNNNNNATCARDDYYAASRWYAMANAKWYYYKB

A.t.    AA--ATTTTA--ATGCAC-ATGTAATCAT------AGTTT------AGCACAATTCAAAA
L.a.    AATGATCTAACGATGCT--ATTTAATATTCGGATCAGTATTCTTAAATAAGAATATAAAA
B.n.    AAACACTTCATCTAGCTCAATATGGTATG------AGTTGGCATACAT-AGAAG-CAAAA
         *   *  *    **  *  **  *         ***    *  *    *   *  *****

Con.4   AANNAYYTHANNWWGCWNNATDTRRTMWKNNNNNNAGTWKNNNNNNAKNASAAKNYAARA

A.t.    ATAATGTAGTA-TTAAAGACAGAAATTTGTA--GACTTTTTT----TTGGCGT-TAAAGG
L.a.    CTAATTCAATAGTTACAGATAAAAACTTATATAGACTTTTTTAT--TTGGAATATAAAAG
B.n.    GGAAGGATGAA-GAAAGGTAATAAAGTTTGGCAGATTGCTTTAGGGTCAGGCTTTAAGTG
         *    *     *  *  * ***  **    ***   *    *      ***  * *

Con.4   VKAAKKHWRWANKWAMRGWHADAAABTTDKRNNGAYTKYTTTNNNNTYRGVVTNTAARDG

A.t.    AA----------------GACTAAGTTTATA-CGT----------ACATTT-TATTTAAGT
L.a.    TATCAATATATTATA-GACAATATTTATAACGTTAAAAATACAATATTTATATTTTTTAT
B.n.    TAACAGTGCAGTTTGGGTGGCTCTAAACAATGTCAAAGCTTCGACAAATAGTCCTTGGGA
           *  *   *      *   *  **  **  *    *     **  **  **

Con.4   WANNNNNNNNNNNNNNNGWSDMWVTWWAYANYGTHNNNNNNNNNNAYAWWTNKWYYTTDDRW

CE1
A.t.    GGA--------AAACCGAAATT--[TTCCATCGA]AATATATGA--ATTT-AGTATAT----
L.a.    ATATTTATTTCAAATTGAAAAGCATTACTTCTATCGAAATGA--ATTTTAGTATATTAAT
B.n.    ACACT------GCATCGACAGATACCCGGTCAAAATTGATTCTGATTCAGGTAAGTCAGA
         * *        *  **  *    *   **  *    **  ***   *  *

Con.4   RBAYTNNNNNNNRMAYYGAYADDYAYYMSDTCDAWMKWDATKMNNATTYNRGTAWRTNNNN

G-box2
A.t.    --ATATTTCTGCAAT------GTACTATTTT GCTATTTTGC AA-CTTTCAGTGGACTAC
L.a.    TAATATTTTTTTAATC-----GGACTACTTTCCTATTTTGGCAC-CTTTCATCTGACTAC
B.n.    GACTCGTGTCCAAAACGGTCGGTCCTAATAAACGATGTTTGCTCTCTTTCGTTT--CTTT
         *  *    **  *    *  *** *    *   ** **  *  **  * ***

Con.4   NNMTMKTKYYBHAAWNNNNNNGKMCTAHTWWVCKATKTTKGCWMNCTTTCRKYKNNCTWY

G-box1
A.t.    TACTTTATTACAATGTGT--ATGGATGC-ATGAG---TTTGAGTA-TACACATGTCTAAA
L.a.    TAATTTATTTCAATGTGT--ATGCATGC-ATGAG---CATGAGTAATACACATGTCTATA
B.n.    TTATTTGTTATAATAATTTGATGGCTACGATGTTTCTCTTGTTTGTTATGAATAAAGAAT
         * ***  *  ***  *     ***  *  **       ***      *    *

Con.4   TWMTTTRTTWYAATRWKTNNATGSMTRCNATGWKNNNYWTGWKTRWTAYRMATRHMKAWW

A-300      EM1 ABA
A.t.    TGCATGCT-TTGCAAAACGTAACGGACC-ACAAAAGAGGATCCA TGCAAATACATCTCAT
L.a.    TAAATGCA-T-GTAAAACGTAACGGACC-ACAAAAGTGGATCCATACAAATACATCTCAT
B.n.    GCAATGGTGTTCTAGTATTTGATTGTTTTACATGTATGTATCTCTT-ATTTACATGAAAT
         ***    *    *   *   *     *    ***  *  *      *  ****   **

Con.4   KVMATGSWNTNSYARWAYKTRAYKGWYYNACAWRWRWGKATCYMTDNAWWTACATSWMAT

A.t.    AGC-TTCCTCCATTATTTTCCGACACAAA-CAGAGCA---
L.a.    CGC-ACCCTC--------TCCGACACAAAACTGAACA---
B.n.    TTTTAAACGCC-------TAAAAAAAAAAACGGAATTCCG
         *           *     * ***    **

Con.4   HKYNWHMCKCNNNNNNNNTMMRAMAMAAANCDGARYWNNN
```

FIG. 4C

ALIGNMENT OF *A.t.* AND *L.a.* FAE1 PROMOTERS
CLUSTAL W (1.74) MULTIPLE SEQUENCE ALIGNMENT

```
A.t.    ------------------------------------------------ACTCATAA
L.a.    CGCCGGGGAGTTTCAGCTTAACCGGTAAAATTGGCCTGTACATATATTTACCACTGAGTA
                                                        *** *
Con.5                                                   ACTSAKWA

A.t.    AAACTAGTAGAT--TGGTTGGTTGGTTTCCA--TGTACCAGAAGGCTTACCCTATTAGTT
L.a.    AAGACATCAGTTAATGATTTGTTGTTACTCAATTGGGCTAAGTGTATTATTATATGTGTT
        **   *  ** *  ** **  **  *****  *  **  **  * *  *  * *** ** ***  ***
Con.5   AARMYAKYAGWTNNTGRTTKGTTGKTWYYCANNTGKRCYARRWGKMTTAYYMTATKWGTT

A.t.    GAAAGTTGAAACTTTGTTCCCTACTCAATTCCTAGTTGTGTAAATGT---ATGTATATGT
L.a.    GTATATAATAAAGGTAGAACGTAA--ATTTACTAAGAATGTGTTTTTCCAATGTGATTGC
        *  *  *  **  *  *  ** **  * ** ***  ***  * *  **** **
Con.5   GWAWRTWRWAAMKKTRKWMCSTAMNNAWTTMCTARKWRTGTRWWTKTNNNATGTRWWTGY

A.t.    AAT---GCGTATAAAACGTAGTACTTAAATGACTAGGAGTGGTTCTTGAGACCGATGAGA
L.a.    TCTTTGGCCTCTTAGGTTTGAATCCTACTCGAGAAG-ACTAATTTTAATTTACTGGCAAA
           *  ** **   *   *  **   *  * ** **    *       **  **   *   **
Con.5   WMTNNNGCSTMTWARRYKTRRWWCYTAMWYGASWAGNASTRRTTYTWRWKWMCKRKSARA

A.t.    GATGGGAGCAGAACTAAAGATGATGACATAATTA------AGAACGAATTTGAAAGG-CT
L.a.    AATAGAAATCAATTTATAAGTGTTTAAACAAATCGATGGTATAACTGATTAGTGATCACT
         ** *   *    *  **   *  * **     * * **       ***  *    *  **
Con.5   RATRGRARYMRAWYTAWARRTGWTKAMAYAAWTMNNHNNNNAKAACKRATTWGWRAKSNCT

A.t.    CTTAGGTTTGAATCCTATTCGAGAATGTTTTTGTCAAAGATAGTGGCGATTTTGAACCAA
L.a.    CTTAGGTTTTGATCCAACTCGAGTATTGAGTATTGAACGCTT-------TTTTTAAATAA
        *********  *****  *******  *  * ****    * **        ****  **  **
Con.5   CTTAGGTTTKRATCCWAYTCGAGWATKKWKTWKTSAAMGMTWNNNHNNNNTTTTKAAMYAA

A.t.    AGAAAACATTTAAAAAATCAGTATCCGGTTAC----GTTCATGCAAATAGAAAGTGGTCT
L.a.    AATCTTGATTTTTAAATTGGTTTTTTGAGTAAAAAAGTTCTTAATATTTCTCTTTGTTT
        *    *    *  *** ***   *    *  * *     *     ***     *  *     *  *
Con.5   ARWMWWSATTTWWAAAWTSRKTWTYYGRKTAMNNNNGTTCHTRMWAWTWKMWMKTKGTTT

A.t.    A---GGATCTGATTGTAATTTTAGA--CTTAAAGAGTCTC--TTAAGATTCAATCCTGGC
L.a.    TAATGGGTTTGTTTTGCATTTTATAAGCTTAATT---CTAATTTAATATTTTATCTATCA
        *  * ** ** *  ** ** ***   *****  *   ***  *******  *  *** **
Con.5   WNNNGGRTYTGWTTKKMATTTTAKANNCTTAAWKWKTCTMNNTTAAKATTYWATCYWKSM

A.t.    T-GTGTACAAAACTACAAATAATATA----TTTTAGACTATTTGGCCTTAACTAAACTTC
L.a.    TCGTCCGTAAAGTTTTATTTGGCACAAACTTGTTTACTTTTCTACCTTA--TAATTTGG
        *  **  **    *  *  *   *  *    *  **  ***  *  ****   ** *
Con.5   TNGTSYRYAAARYTWYAWWTRRYAYANNNNTKTTWKACTWTTYKRCCTTANNTAAWYTKS

A.t.    CA-CTCATTATTTACTGAGGTTAGAGAATAGACTTGCGAATAAACACATTCCCGAGAAAT
L.a.    GAACTGGTTGAGT-CAAAGCGTACCGGACAAATATGTTT-TATATTCTTATTTAAGAATT
         *  **  **   * *    *  *    * *    *   * *  **      *****  *
Con.5   SANCTSRTTRWKTNCHRAGSKTASMGRAYARAYWTGYKWNTAWAYWCWTWYYRAGAAWT

-400
A.t.  -432  ACTCATGATCCCATAATTAGTCAGAGGGTATG---------GCAATCAGATCTAAGAACA
L.a.         AACACTCATCTCATAATTAGTCAGAGGCTAGGGAGATTCAGCCAATCAATGCTAACAACA
               *   ************************  **                ******   *****  ****
Con.5        AMYMMTSATCYCATAATTAGTCAGAGGSTAKGNNNNNNNNNCCAATCARWKCTAASAACA
```

FIG. 5A

ALIGNMENT OF *A.t.* AND *L.a.* FAE1 PROMOTERS *(CONTINUED)*

```
A.t.    -381   CACATTCCCTCAA--ATTTTA--ATGCACATGTAATCAT------AGTTT------AGCA
L.a.           AA-ATTCTCTTAATGATCTAACGATGCT-ATTTAATATTCGGATCAGTATTCTTAAATAA
                * **** ** **   ** * * ***** ** ****  *    *** *    *   *  *
Con.5          MANATTCYCTYAANNATYTWANNATGCWNATKTAATMWTNNNNNNAGTWTNNNNNNAKMA

A.t.    -337   CAATTCAAAAATAATGTAGTA-TTAAAGACAGAAATTTGTA--GACTTTTTT--TTGGCG
L.a.           GAATATAAAACTAATTCAATAGTTACAGATAAAAACTTATATAGACTTTTTTATTTGGAA
                ***  **** ****  * ** *** *** **   * **  *  *********  ****
Con.5          SAATWYAAAAMTAATKYARTANTTAMAGAYARAAAYTTRTANNGACTTTTTTNNTTGGMR

A.t.    -282   T-TAAAGGAA------------GACTAAGTTTATA-CGT----------ACATTT-TAT
L.a.           TATAAAAGTATCAATATATTATAGACAATATTTATAACGTTAAAAATACAATATTTATAT
                * ****  *             *** ** *****  ***          * **** ***
Con.5          TNTAAARGWANNNNNNNNNNNNNGACWAWRTTTATANCGTNNNNNNNNNNNAYATTTNTAT

A.t.    -247   TTTAAGTGGA--------AAACCGAAATT--TTCCATCGAAATATATGAATTT-AGTATA
L.a.           TTTTTATATATTTATTTCAAATTGAAAAGCATTACTTCTATCGAAATGAATTTTAGTATA
                *** *   *     * *  *** * ** **  * ***  * **** **  *  **  **
Con.5          TTTWWRTRKANNNNNNNNNNAAAYYGAAAWKNNTTMCWTCKAWMKAWATGAATTTNAGTATA

A.t.    -198   T------ATATTTCTGCAAT-GTACTATTTGCTATTTTGGCAACTTTCAGTGGACTACT
L.a.           TTAATTAATATTTTTTTAATCGGACTACTTTCCTATTTTGGCACCTTTCATCTGACTACT
                *      ****** * ***  **  * ***   ************ ******   ******
Con.5          TNNHNNNATATTTYTKYAATNGKACTAYTTTSCTATTTTGGCAMCTTTCAKYKGACTACT

A.t.    -145   ACTTTATTACAATGTGTATGGATGCATGAGTTTGAGTA-TACACATGTCTAAATGCATGC
L.a.           AATTTATTTCAATGTGTATGCATGCATGAGCATGAGTAATACACATGTCTATATAAATGC
                * ****** ************ ******** ****** ************* **  ***
Con.5          AMTTTATTWCAATGTGTATGSATGCATGAGYWTGAGTANTACACATGTCTAWATRMATGC

A.t.    -86    TTTGCAAAACGTAACGGACCACAAAAGAGGATCCATGCAAATACATCTCATAGCTTCCTC
L.a.           AT-GTAAAACGTAACGGACCACAAAAGTGGATCCATACAAATACATCTCATCGCACCCTC
                *  * *************************** ********** ****** **  ****
Con.5          WTNGYAAAACGTAACGGACCACAAAAGWGGATCCATRCAAATACATCTCATMGCWYCCTC

A.t.    -26    CATTATTTTCCGACACAAA-CAGAGCA
L.a.           --------TCCGACACAAAACTGAACA
                        *********  * *   **
Con.5          NNNNNNNNTCCGACACAAANCWGARCA
```

FIG. 5B

Alignment of B.n. and L.a. FAE1 promoters
CLUSTAL W (1.81) multiple sequence alignment

```
BnFAE1   GGTTGGGCAAATCTGACTTCACCAAAGAAACAACTCGAGTCGTTATCCATCTCCTCATAA  60
LaFAE1   ------------------------------------------------------------

BnFAE1   CCATCGCTCCACTCTTTGCCTTCACCGTTTTCGGTTCGGTTCTCTACATCGCAACCCGGC 120
LaFAE1   ------------------------------------------------------------

BnFAE1   CCAAACCGGTTTACCTCGTTGAGTACTCATGCTACCTTCCACCAACGCATTGTAGATCAA 180
LaFAE1   ------------CGCCGGGGAGT-TTCAGCTTAACCGGTAAAATTGGCCTGTACATATA   46
                     *  **  ****   ***   **          *    ****  **    *

BnFAE1   GTATCTCCAAGGTCATGGATATCTTTTATCAAGTAAGAAAAGCTGATCCTTCTCGGAACG 240
LaFAE1   TTTACCACTGAGT-AAAGACATCAGTTAATGATTT-----GTTGTTACTCAATTGGGCT   99
          *   *    **   **   ** ***  **   *          *  ** *  **     * *

BnFAE1   GCACGTGCGATGACTCGTCGTGGCTTGACTTCTTGAGGAAGATTCAAGAACGTTCAGGTC 300
LaFAE1   AAGTGTATTATTATATGTGTTG------TATATAATAAAGGT---AGAACGT--AAATT  147
          **   **  *    ** **         *    **  ***** *  *******  *   *

BnFAE1   TAGGCGATGAAACTCACGGGCCCGTGGGGCTGCTTCAGGTCCCTCCCCGGAAGACTTTTG 360
LaFAE1   TA--CTAAGAATGTGTTTTTCCAATGTGATTGCTCTTTGGCCTCTTAGGTTTGAATCCTA 205
          **    *  *     *     **         *    **   **  **  *  **  * *

BnFAE1   CGGCGGCGCGTGAAGAGACGGAGCAAGTTATCATTGGTGCGCTAGAAAATCTATTCAAGA 420
LaFAE1   CT-------CGAGAAGACTAATTTTAAT-TTACTGGCAAAAATAGAAATCAATTTATAA  256
          *         **  ****   *    *  * * ***         *****   **  *  *

BnFAE1   ACACCAACGTTAACCCTAAAGATATAGGTATACTTGTGGTGAACTCAAGCATGTTTAATC 480
LaFAE1   GTGTTTAAACAAATC--GATGGTATAACTG-ATTAGTGATCACTCTTAGGTT--TTGATC 311
                *  **  *    * * ****     *   *  *  *  **        **  **  ***

BnFAE1   CAACTCCATCGCTCTCCGCGATGGTCGTTAACACTTTCAAGCTCCGAAGCAACGTAAGAA 540
LaFAE1   CAACTCGAGTATTG--------AGTATTGAACGCTTT-----TTTTAAATAAAATCTTGA 358
         ******  *       *           **  *   ****      *  **  **   *  *

BnFAE1   GCTTTAACCTTGGTGGCATGGGTTGTAGTGCCGGCGTTATAGCCATTGATCTAGCAAAGG 600
LaFAE1   TTTTTAAA-TTGGTTTTTTGAGTAAAAAAGTTCTTAATATTTTCTCTT-TGTTTTAATGG 416
           ****   *****         **    **   *   **   *  *       * **** **

BnFAE1   ACTTGTTGCATGTCC-ATAAAAATACGTATGCTCTTGTGGTGAGCACAGAGAACATCACT 659
LaFAE1   GTTTGTTTTGCATTTTATAAGCTTAATTTTTCTAATTTAAT-ATTTTATCTATCATCGTC 475
          *****    *     *  **  *       **    *    *  *   **  *  *****

BnFAE1   TATAACATTTACGCTGGTGATAATAGGTCCATGATGGTTTCAAATTGCTTGTTCCGTGTT 719
LaFAE1   CGTAAAGTTT----------TATTTGGCACAAACTTGTTTTA---CTTTTCTACCTTATA 522
          *** ***          **  *   **   **   ****       **  * **  *  *

BnFAE1   GGTGGGGCCGCTATTTTGCTCTCCAACAAGCCTGGAGATCGTAGACGGTCCAAGTACGAG 779
LaFAE1   ATTTGGGA-ACTGGTTGAGTCA-----AAGCGTACCGGACAAATATGTTTTATATTC--- 573
            *  ***   ** **  *  **        ****          *         *  *

BnFAE1   CTAGTTCACACGGTTCGAACGCATACCGGAGCTGACGACAAGTCTTTTCGTTGCGTGCAA 839
LaFAE1   -TTATTTA-AGAATTAACACTCATCTCATAATTAGTCAGAGGC-------TAGGGAGATT 624
          *  **  *   ** **    **    *   *     **    *              *  *

BnFAE1   CAAGGAGACGATGAGAACGGCAAAATCGGAGTGAGTTTGTCCAAGGACATAACCGATGTT 899
LaFAE1   CAGCCAATCAATGCTAACAACAAAATTCTCTTAA--TGATCTAACGATGCTATTTAATAT 682
         **   *  *  *** ***    *****             *    **      *   *  *
```

FIG. 7A

Alignment of *B.n.* and *L.a.* FAE1 promoters

```
BnFAE1  GCTGGTCGAACGGTTAAGAAAAACATAGCAACGTTGGGTCCGTTGATTCTTCCGTTA-AG 958
LaFAE1  TCGGATCAGTATTCTTAAATAAGAATATAAA-----------ACTAATTCAATAGTTACAG 732
         *  **     *  *  **   ***   **       *   ****      ****  **

BnFAE1  CGAGAAACTTCTTTTTTTCGTTACCTTCATGGGCAAGAAACTTTTCAAAGATAAAATCAA 1018
LaFAE1  ATAAAAACTTATATAGACTTTTTTATTTG-AATATAAAAGTATCAATATATTATAGACA 791
         * ****** * *    **  **  *  *   *  *  ***  *    *   * *  *  *

BnFAE1  ACATTACTACGTCCCGGATTTCAAACTTGCTATTGACCATTTTTGTATACATGCCGGAGG 1078
LaFAE1  ATATTTATA------ACGTTAAAAATACAATATTTATATTTTTATATATTTATTTCAAA 845
         * ***  **       **   ***    ****  *  *****  ****    *       *

BnFAE1  CAGAGCCGTGATTGATGTGCTAGAGAAGAACCTAGCCCTAGCACCGATCGATGTAGAGGC 1138
LaFAE1  TTGAAAAGCATTACTTCTATCGAAATGAATTTTAGT----ATATTAATTAATATTTTTTT 901
         **   *   ** *      *  ** *  *  ****     *   **  **  * *  *

BnFAE1  ATCAAGATCAACGTTACATAGATTTGGAAACACTTCATCTAGCTCAATATGGTATGAGTT 1198
LaFAE1  AATCGGACTACTTTCCTAT----TTTGGCACCTTTCATCTGACT-------------ACT 944
         * **  * * * *  **    ** * **  ****** **              *

BnFAE1  GGCATACATAGAAGCAAAAGGAAGGATGAAGAAAGGTAATAAAGTTTGGCAGATTGCTTT 1258
LaFAE1  AATTTATTTCAATGTGTATGCATGCATGAGCATGAGTAATA--------CACATGTCTAT 996
         **   *  **  * *  * * *   ****   *   ****          **  **  *

BnFAE1  AGGGTCAGGCTTTAAGTGTAACAGTGCAGTTTGGGTGGCTCTAAACAATGTCAAAGCTTC 1318
LaFAE1  ATAAATGCATGTAAAACGTAACGG-ACCACAAAAGTGGATCCATACAAATACATCTCATC 1055
         *      *  ** ***** *  *      ***  ** * *  ****    *  * **

BnFAE1  GACAAATAGTCCTTGGGAACACTGCATCGACAGATACCCGGTCAAAATTGATTCTGATTC 1378
LaFAE1  G-CACCCTCTCCGACACAAAACTGAACA-------------------------------- 1082
         *  ** *** **   *  *   ***  *

BnFAE1  AGGTAAGTCAGAGACTCGTGTCCAAAACGGTCGGTCCTAATAAACGATGTTTGCTCTCTT 1438
LaFAE1  ------------------------------------------------------------

BnFAE1  TCGTTTCTTTTTATTTGTTATAATAATTTGATGGCTACGATGTTTCTCTTGTTTGTTATG 1498
LaFAE1  ------------------------------------------------------------

BnFAE1  AATAAAGAATGCAATGGTGTTCTAGTATTTGATTGTTTTACATGTATGTATCTCTTATTT 1558
LaFAE1  ------------------------------------------------------------

BnFAE1  ACATGAAATTTTTAAACGCCTAAAAAAAAAAACGGAATTCCG 1600
LaFAE1  ------------------------------------------
```

FIG. 7B

ALIGNMENT OF B.n. AND A.t. FAE1 PROMOTERS
CLUSTAL W (1.81) MULTIPLE SEQUENCE ALIGNMENT

```
AtFAE1    ------------------------------------------------------------
BnFAE1    GGTTGGGCAAATCTGACTTCACCAAAGAAACAACTCGAGTCGTTATCCATCTCCTCATAA 60

AtFAE1    ------------------------------------------------------------
BnFAE1    CCATCGCTCCACTCTTTGCCTTCACCGTTTTCGGTTCGGTTCTCTACATCGCAACCCGGC 120

AtFAE1    ------------------------------------------------------------
BnFAE1    CCAAACCGGTTTACCTCGTTGAGTACTCATGCTACCTTCCACCAACGCATTGTAGATCAA 180

AtFAE1    ------------------------------------------------------ACTCATAAAA 10
BnFAE1    GTATCTCCAAGGTCATGGATATCTTTTATCAAGTAAGAAAAGCTGATCCTTCTCGGAACG 240
                                                              ***  **

AtFAE1    ACTAGTAGATTGGTTGGT--TGGTTCCATGTACCAGAAGGCTT-----ACCCTATTAGT 63
BnFAE1    GCACGTGCGATGACTCGTCGTGGCTTGACTTCTTGAGGAAGATTCAAGAACGTTCAGGTC 300
            *  **    **  *  **  ***  **   **  *  * **       **   *

AtFAE1    TGAAAGTTGAAACTT-TGTTCCCTACT--CAATTCCTAGTTGTGTAAATGTATGTATATG 120
BnFAE1    TAGGCGATGAAACTCACGGGCCCGAGGGGCTGCTTCAGGTCCCTCCCCGGAAGACTTTTG 360
          *   *  ******  *   * ***  *   * * *  **              * *  **

AtFAE1    TAATG-CGTATAAAACGTAGTACTTAAATGACTAGGAGTGGTTCTTGAGACCGATGAGAG 179
BnFAE1    CGGCGGCGCGTGAAGAGACGGAGC-AAGTTATCATTGGTGCGCTAGAAAATCTATTCAAG 419
            * **  * *    **      * * ** *   *      * *       *   **  **

AtFAE1    A-----TGGGAGCAGAACTAAAGATGATGACATAATTAAGAACGAATTTGAAAGGCTCTTA 235
BnFAE1    AACACCAACGTTAACCCTAAAGATATAGGTATACTTGTGG-TGAACTCAAGCATGTTTAA 478
          *            *   *******   ****  **  *  *   **   *  *  * *

AtFAE1    GGTTTGAATCCTATTCGAGAATGTTTTTGTCAAAGATAGTGGCGA-TTTTGAACCAAAGA 294
BnFAE1    ---TCCAACTCCATCGCTCTCCGCGATGGTCGTTAACACTTTCAAGCTCCGAAGCAACGT 535
               *  *   * **  *   *    *** * *   *  *   * ***  *   *

AtFAE1    AAACATTTAAAAAATCAGTATCC--GGTTAC-GTTCATGCAA-ATAGAAAGTGGTCTAGG 350
BnFAE1    AAGAAGCTTTAACCTTGGTGGCATGGTTGTAGTGCCGGCGTTATAGCCATTGATCTAGC 595
          **  *   *  **  * **  * *   ****  * *  *  ****  *  ** *****

AtFAE1    ATCTGATTGTAATTTTAGACTTAAAGAGTCTCTTAAGATTCAATCCTGGCTGTGTACAAA 410
BnFAE1    AAAGGACTT--GTTGCATGTCCATAAAAATACGTATGCTCTTGTGGTGAGCACAGAGAAC 653
          *   **  **   * *    * *   * *    *  * *  *   * * *   *  **

AtFAE1    ACTACAAATAATATAT---TTTAGACTATTTGGCCTTAACTAAACTTCCACTCATTATTT 467
BnFAE1    ATCACTTATAACATTTACGCTGGTGATAATAGGTCCATGATGGTTTCAAATTGCTTGTTC 713
          *  **  *****  **   *         ** **  **  *         ** ** **

AtFAE1    ACTGAGGTTAGAGA-ATAGACTTGCGAATAAACACATTCCCGAGAAATACTCATGATCCC 526
BnFAE1    CGTGTTGGTGGGGCCGCTATTTTGCTCTCCAACAAG--CCTGGAGATCGTAGACGGTCCA 771
           **    **        *** **** *     *  *   **  **   ** *   **

AtFAE1    ATAATTAGTCAGAGGGTATG---CCAATCAGATCTAAGAAC[ACACATTCCCTG]AAATTTTA 584
BnFAE1    AGTACGAGCTAGTTCACACGGTTCGAACGCATACCGGAGCTGACGACAAGTCTTTTCGTT 831
                                                    CE3
             *  *  * **          *    * *    *   *  **    **   *

AtFAE1    ATGCACATGTAATCATAGTTTAGCACAATTCAAAAATAATGTAGTATTAAAGACAGAAAT 644
BnFAE1    GCGTGCAACAAGGAGACGATGAGAACGGCAAAATCGGAGTGAGTTTGTCCAAGGACATAA 891
            * **  *   *   *  **   *          **    *   *  * * *
```

FIG. 8A

ALIGNMENT OF *B.n.* AND *A.t. FAE1* PROMOTERS *(CONTINUED)*

```
AtFAE1    TTGTAGACTTTTTTTTGGCGTTAAAGGAAGACTAAG------TTTATACGTACATTTTAT 698
BnFAE1    CCGATGTTGCTGGTCGAACGGTTAAGAAAAACATAGCAACGTTGGGTCCGTTGATTCTTC 951
            *  *   *  *   ** * *** ** ** **        *   * *** *** *

AtFAE1    T-TTAAGTGGAAAACCGAAATTTTCCAT------CGAAATATATGAATTTAGTATATATA 751
BnFAE1    CGTTAAGCGAGAAACTTCTTTTTTTTCGTTACCTTCATGGGCAAGAAACTTTTCAAAGATA 1011
           *****  *  ****  ****  * *      *      *  ** **   * * ***
                                           G box 2
AtFAE1    TTTCTGCAATGTACTATTTTGCTATTTTGG[CAACTTT]CAGTGGACTACTACTTTAT-TAC 810
BnFAE1    AAATCAAACATTACTACGTCCCGGATTTCA-AACTTGCTATTGACCATTTTTGTATACAT 1070
            *   *****  *  *  ***  ***** *   *** * *  * * *  ** *
                                            G-box 1
AtFAE1    AATGTGTATGGATGCATGAGTT-TGAGTATA[CACATGT]CTAAATGCATGCTTTGCAAAAC 869
BnFAE1    GCCGGAGGCAGAGCCGTGATTGATGTGCTAGAGAAGAACCTAGCCCTAGCACCGATCGAT 1130
            *       **  * *** *   ** *         *   *   *  **   *

AtFAE1    GTAACGG-ACCACAAAAGAGGATCCAT------GCAAATACATCTCATAGCTTCCTCCAT 922
BnFAE1    GTAGAGGCATCAAGATCAACGTTACATAGATTTGGAAACACTTCATCTAGCTCAATATGG 1190
          ***  **  *  **   *      *       *  *** ** **  **   *

AtFAE1    TATTTTCCGACACAAACAGA-GCA------------------------------- 945
BnFAE1    TATGAGTTGGCATACATAGAAGCAAAAGGAAGGATGAAGAAAGGTAATAAAGTTTGGCAG 1250
          ***         *   * *  ***   ***

AtFAE1    -----------------------------------------------
BnFAE1    ATTGCTTTAGGGTCAGGCTTTAAGTGTAACAGTGCAGTTTGGGTGGCTCTAAACAATGTC 1310

AtFAE1    -----------------------------------------------
BnFAE1    AAAGCTTCGACAAATAGTCCTTGGGAACACTGCATCGACAGATACCCGGTCAAAATTGAT 1370

AtFAE1    -----------------------------------------------
BnFAE1    TCTGATTCAGGTAAGTCAGAGACTCGTGTCCAAAACGGTCGGTCCTAATAAACGATGTTT 1430

AtFAE1    -----------------------------------------------
BnFAE1    GCTCTCTTTCGTTTCTTTTTATTTGTTATAATAATTTGATGGCTACGATGTTCTCTTGT 1490

AtFAE1    -----------------------------------------------
BnFAE1    TTGTTATGAATAAAGAATGCAATGGTGTTCTAGTATTTGATTGTTTTACATGTATGTATC 1550

AtFAE1    -----------------------------------------------
BnFAE1    TCTTATTTACATGAAATTTTTAAACGCCTAAAAAAAAAAACGGAATTCCG 1600
```

FIG. 8B

SEQUENCE LISTING

```
<160> NUMBER OF SEQ ID NOS: 23

<210> SEQ ID NO 1
<211> LENGTH: 12
<212> TYPE: DNA
<213> ORGANISM: Arabidopsis thaliana
<220> FEATURE:
<221> NAME/KEY: misc_signal
<222> LOCATION: (1)..(12)
<223> OTHER INFORMATION: CE3 element at 381-369 bp

<400> SEQUENCE: 1
acacattccc tc                                                          12

<210> SEQ ID NO 2
<211> LENGTH: 12
<212> TYPE: DNA
<213> ORGANISM: Artificial sequence
<220> FEATURE:
<221> NAME/KEY: misc_signal
<222> LOCATION: (1)..(12)
<223> OTHER INFORMATION: consensus sequence

<400> SEQUENCE: 2
acgcgtgtcc tc                                                          12

<210> SEQ ID NO 3
<211> LENGTH: 25
<212> TYPE: DNA
<213> ORGANISM: Artificial sequence
<220> FEATURE:
<221> NAME/KEY: primer
<222> LOCATION: (1)..(25)
<223> OTHER INFORMATION: AtproFW

<400> SEQUENCE: 3
ctagtagatt ggttggttgg tttcc                                            25

<210> SEQ ID NO 4
<211> LENGTH: 27
<212> TYPE: DNA
<213> ORGANISM: Artificial sequence
<220> FEATURE:
<221> NAME/KEY: primer
<222> LOCATION: (1)..(27)
<223> OTHER INFORMATION: AtproRV

<400> SEQUENCE: 4
tgctctgttt gtgtcggaaa ataatgg                                          27
```

-continued

```
<210> SEQ ID NO 5
<211> LENGTH: 27
<212> TYPE: DNA
<213> ORGANISM: Artificial sequence
<220> FEATURE:
<221> NAME/KEY: primer
<222> LOCATION: (1)..(27)
<223> OTHER INFORMATION: AP1

<400> SEQUENCE: 5
ggatcctaat acgactcact atagggc                               27

<210> SEQ ID NO 6
<211> LENGTH: 25
<212> TYPE: DNA
<213> ORGANISM: Artificial sequence
<220> FEATURE:
<221> NAME/KEY: primer
<222> LOCATION: (1)..(25)
<223> OTHER INFORMATION: Bnwalk1

<400> SEQUENCE: 6
aaagagtgga gcgatggtta tgagg                                 25

<210> SEQ ID NO 7
<211> LENGTH: 18
<212> TYPE: DNA
<213> ORGANISM: Artificial sequence
<220> FEATURE: <221>   primer
<222> LOCATION: (1)..(18)
<223> OTHER INFORMATION: AP2

<400> SEQUENCE: 7
ctatagggct cgagcggc                                         18

<210> SEQ ID NO 8
<211> LENGTH: 25
<212> TYPE: DNA
<213> ORGANISM: Artificial sequence
<220> FEATURE:
<221> NAME/KEY: primer
<222> LOCATION: (1)..(25)
<223> OTHER INFORMATION: Bnwalk2

<400> SEQUENCE: 8
cggaaagaag caaaggttga aaagg                                 25

<210> SEQ ID NO 9
<211> LENGTH: 24
<212> TYPE: DNA
<213> ORGANISM: Artificial sequence
<220> FEATURE:
<221> NAME/KEY: primer
<222> LOCATION: (1)..(24)
<223> OTHER INFORMATION: Lawalk1

<400> SEQUENCE: 9
gatcgtttgt ggtaagacga gagc                                  24

<210> SEQ ID NO 10
<211> LENGTH: 24
<212> TYPE: DNA
<213> ORGANISM: Artificial sequence
<220> FEATURE:
<221> NAME/KEY: primer
<222> LOCATION: (1)..(24)
<223> OTHER INFORMATION: Lawalk2

<400> SEQUENCE: 10
```

```
gtcagtggga agaaacagag gttg                                           24

<210> SEQ ID NO 11
<211> LENGTH: 25
<212> TYPE: DNA<213>  Artificial sequence
<213> ORGANISM:
<220> FEATURE:
<221> NAME/KEY: primer
<222> LOCATION: (1)..(25)
<223> OTHER INFORMATION: BnproFW

<400> SEQUENCE: 11
ctgacttcac caaagaaaca actcg                                          25

<210> SEQ ID NO 12
<211> LENGTH: 26
<212> TYPE: DNA
<213> ORGANISM: Artificial sequence
<220> FEATURE:
<221> NAME/KEY: primer
<222> LOCATION: (1)..(26)
<223> OTHER INFORMATION: BnproRV

<400> SEQUENCE: 12
cggaattccg tttttttttt taggcg                                         26

<210> SEQ ID NO 13
<211> LENGTH: 23
<212> TYPE: DNA
<213> ORGANISM: Artificial sequence
<220> FEATURE:
<221> NAME/KEY: primer
<222> LOCATION: (1)..(23)
<223> OTHER INFORMATION: LaproFW

<400> SEQUENCE: 13
cagcttaacc ggtaaaattg gcc                                            23

<210> SEQ ID NO 14
<211> LENGTH: 23
<212> TYPE: DNA
<213> ORGANISM: Artificial sequence
<220> FEATURE:
<221> NAME/KEY: primer
<222> LOCATION: (1)..(23)
<223> OTHER INFORMATION: LaproRV

<400> SEQUENCE: 14
tgttcagttt tgtgtcggag agg                                            23

<210> SEQ ID NO 15
<211> LENGTH: 393
<212> TYPE: DNA
<213> ORGANISM: Artificial sequence
<220> FEATURE:
<221> NAME/KEY: promoter
<222> LOCATION: (1)..(393)
<223> OTHER INFORMATION: transcriptional regulatory region

<400> SEQUENCE: 15
agatctaaga acacacattc cctcaaattt taatgcacat gtaatcatag tttagcacaa     60
ttcaaaaata atgtagtatt aaagacagaa atttgtagac ttttttttgg cgttaaagga    120
agactaagtt tatacgtaca ttttatttta agtggaaaac cgaaattttc catcgaaata    180
tatgaattta gtatatatat ttctgcaatg tactattttg ctatttttggc aactttcagt    240
```

```
ggactactac tttattacaa tgtgtatgga tgcatgagtt tgagtataca catgtctaaa      300
tgcatgcttt gcaaaacgta acggaccaca aaagaggatc catgcaaata catctcatag      360
cttcctccat tattttccga cacaaacaga gca                                   393
```

<210> SEQ ID NO 16
<211> LENGTH: 934
<212> TYPE: DNA
<213> ORGANISM: Artificial sequence
<220> FEATURE:
<221> NAME/KEY: promoter
<222> LOCATION: (1)..(934)
<223> OTHER INFORMATION: transcriptional regulatory region

<400> SEQUENCE: 16

```
ctagtagatt ggttggttgg tttccatgta ccagaaggct taccctatta gttgaaagtt       60
gaaactttgt tccctactca attcctagtt gtgtaaatgt atgtatatgt aatgcgtata      120
aaacgtagta cttaaatgac taggagtggt tcttgagacc gatgagagat gggagcagaa      180
ctaaagatga tgacataatt aagaacgaat ttgaaaggct cttaggtttg aatcctattc      240
gagaatgttt ttgtcaaaga tagtggcgat tttgaaccaa agaaaacatt taaaaaatca      300
gtatccggtt acgttcatgc aaatagaaag tggtctagga tctgattgta attttagact      360
taaagagtct cttaagattc aatcctggct gtgtacaaaa ctacaaataa tatattttag      420
actatttggc cttaactaaa cttccactca ttatttactg aggttagaga atagacttgc      480
gaataaacac attcccgaga atactcatg atcccataat tagtcagagg gtatgccaat       540
cagatctaag aacacacatt ccctcaaatt ttaatgcaca tgtaatcata gtttagcaca      600
attcaaaaat aatgtagtat taagacaga aatttgtaga cttttttttg gcgttaaagg       660
aagactaagt ttatacgtac attttatttt aagtggaaaa ccgaaatttt ccatcgaaat      720
atatgaattt agtatatata tttctgcaat gtactatttt gctatttggg caactttcag      780
tggactacta ctttattaca atgtgtatgg atgcatgagt ttgagtatac acatgtctaa      840
atgcatgctt tgcaaaacgt aacggaccac aaaagaggat ccatgcaaat acatctcata      900
gcttcctcca ttattttccg acacaaacag agca                                  934
```

<210> SEQ ID NO 17
<211> LENGTH: 1588
<212> TYPE: DNA
<213> ORGANISM: Artificial sequence
<220> FEATURE:
<221> NAME/KEY: promoter
<222> LOCATION: (1)..(1588)
<223> OTHER INFORMATION: transcriptional regulatory region

<400> SEQUENCE: 17

```
ctgacttcac caaagaaaca actcgagtcg ttatccatct cctcataacc atcgctccac       60
tctttgcctt caccgttttc ggttcggttc tctacatcgc aacccggccc aaaccggttt      120
acctcgttga gtactcatgc taccttccac caacgcattg tagatcaagt atctccaagg      180
tcatggatat cttttatcaa gtaagaaaag ctgatcsttc tcggaacggc acgtgcgatg      240
actcgtcgtg gcttgacttc ttgaggaaga ttcaagaacg ttcaggtcta ggcgatgaaa      300
ctcacgggcc cgaggggctg cttcaggtcc ctccccggaa gacttttgcg gcggcgcgtg      360
aagagacgga gcaagttatc attggtgcgc tagaaaatct attcaagaac accaacgtta      420
accctaaaga tataggtata cttgtggtga actcaagcat gtttaatcca actccatcgc      480
tctccgcgat ggtcgttaac actttcaagc tccgaagcaa cgtaagaagc tttaaccttg      540
```

```
gtggcatggg ttgtagtgcc ggcgttatag ccattgatct agcaaaggac ttgttgcatg      600
tccataaaaa tacgtatgct cttgtggtga gcacagagaa catcacttat aacatttacg      660
ctggtgataa taggtccatg atggtttcaa attgcttgtt ccgtgttggt ggggccgcta      720
ttttgctctc caacaagcct ggagatcgta gacggtccaa gtacgagcta gttcacacgg      780
ttcgaacgca taccggagct gacgacaagt cttttcgttg cgtgcaacaa ggagacgatg      840
agaacggcaa atcggagtg agtttgtcca aggacataac cgatgttgct ggtcgaacgg       900
ttaagaaaaa catagcaacg ttgggtccgt tgattcttcc gttaagcgag aaacttcttt      960
ttttcgttac cttcatgggc aagaaacttt tcaaagataa aatcaaacat tactacgtcc     1020
cggatttcaa acttgctatt gaccattttt gtatacatgc cggaggcaga gccgtgattg     1080
atgtgctaga gaagaaccta gccctagcac cgatcgatgt agaggcatca agatcaacgt     1140
tacatagatt tggaaacact tcatctagct caatatggta tgagttggca tacatagaag     1200
caaaaggaag gatgaagaaa ggtaataaag tttggcagat tgctttaggg tcaggcttta     1260
agtgtaacag tgcagtttgg gtggctctaa acaatgtcaa agcttcgaca aatagtcctt     1320
gggaacactg catcgacaga tacccggtca aaattgattc tgattcaggt aagtcagaga     1380
ctcgtgtcca aaacggtcgg tcctaataaa cgatgtttgc tctctttcgt ttcttttttat    1440 ttgttataat aatttgatgg ctacgatgtt tctcttgttt gttatgaata agaatgcaa      1500 tggtgttcta gtatttgatt gttttacatg tatgtatctc ttatttacat gaaattttta     1560
aacgcctaaa aaaaaaacg gaattccg                                         1588

<210> SEQ ID NO 18
<211> LENGTH: 1069
<212> TYPE: DNA
<213> ORGANISM: Artificial sequence
<220> FEATURE:
<221> NAME/KEY: promoter
<222> LOCATION: (1)..(1069)
<223> OTHER INFORMATION: transcriptional regulatory region

<400> SEQUENCE: 18
cagcttaacc ggtaaaattg gcctgtacat atatttacca ctgagtaaag acatcagtta      60
atgatttgtt gttactcaat tgggctaagt gtattattat atgtgttgta tataataaag     120
gtagaacgta aatttactaa gaatgtgttt ttccaatgtg attgctcttt ggcctcttag     180
gtttgaatcc tactcgagaa gactaatttt aatttactgg caaaaataga aatcaattta     240
taagtgttta aacaaatcga tggtataact gattagtgat cactcttagg ttttgatcca     300
actcgagtat tgagtattga acgcttttt taaataaaat cttgattttt aaattggttt     360
tttgagtaaa aaagttctta atattttctc tttgttttaa tgggtttgtt ttgcatttta     420
taagcttaat ttttctaatt taatatttta tctatcatcg tccgtaaagt tttatttggc     480
acaaacttgt tttacttttc taccttataa tttgggaact ggttgagtca aagcgtaccg     540
gacaaatatg ttttatattc ttatttaaga attaacactc atctcataat tagtcagagg     600
ctagggagat tcagccaatc aatgctaaca acaaaattct cttaatgatc taacgatgct     660
atttaatatt cggatcagta ttcttaaata agaatataaa actaattcaa tagttacaga     720
taaaaactta tatagacttt tttatttgga atataaaagt atcaatatat tatagacaat     780
atttataacg ttaaaaatac aatatttata tttttttatat atttatttca aattgaaaag     840
cattacttct atcgaaatga attttagtat attaattaat attttttaa tcggactact     900
```

| | |
|---|---|
| ttcctatttt ggcacctttc atctgactac taatttattt caatgtgtat gcatgcatga | 960 |
| gcatgagtaa tacacatgtc tatataaatg catgtaaaac gtaacggacc acaaaagtgg | 1020 |
| atccatacaa atacatctca tcgcaccctc tccgacacaa aactgaaca | 1069 |

<210> SEQ ID NO 19
<211> LENGTH: 972
<212> TYPE: DNA
<213> ORGANISM: Arabidopsis thaliana;
<220> FEATURE:
<221> NAME/KEY: promoter
<222> LOCATION: (1)..(972)
<223> OTHER INFORMATION: FAE1 promoter

<400> SEQUENCE: 19

| | |
|---|---|
| actcataaaa actagtagat tggttggttg gtttccatgt accagaaggc ttaccctatt | 60 |
| agttgaaagt tgaaactttg ttccctactc aattcctagt tgtgtaaatg tatgtatatg | 120 |
| taatgcgtat aaaacgtagt acttaaatga ctaggagtgg ttcttgagac cgatgagaga | 180 |
| tgggagcaga actaaagatg atgacataat taagaacgaa tttgaaaggc tcttaggttt | 240 |
| gaatcctatt cgagaatgtt tttgtcaaag atagtggcga ttttgaacca agaaaaacat | 300 |
| ttaaaaaatc agtatccggt tacgttcatg caaatagaaa gtggtctagg atctgattgt | 360 |
| aattttagac ttaaagagtc tcttaagatt caatcctggc tgtgtacaaa actacaaata | 420 |
| atatatttta gactatttgg ccttaactaa acttccactc attatttact gaggttagag | 480 |
| aatagacttg cgaataaaca cattcccgag aaatactcat gatcccataa ttagtcagag | 540 |
| ggtatgccaa tcagatctaa gaacacacat tccctcaaat tttaatgcac atgtaatcat | 600 |
| agtttagcac aattcaaaaa taatgtagta ttaaagacag aaatttgtag acttttttt | 660 |
| ggcgttaaag gaagactaag tttatacgta catttatttt taagtggaaa accgaaattt | 720 |
| tccatcgaaa tatatgaatt tagtatatat atttctgcaa tgtactattt tgctattttg | 780 |
| gcaactttca gtggactact actttattac aatgtgtatg gatgcatgag tttgagtata | 840 |
| cacatgtcta aatgcatgct ttgcaaaacg taacggacca caaagagga tccatgcaaa | 900 |
| tacatctcat agcttcctcc attattttcc gacacaaaca gagcaatgac gtccgttaac | 960 |
| gttaagctcc tt | 972 |

<210> SEQ ID NO 20
<211> LENGTH: 1790
<212> TYPE: DNA
<213> ORGANISM: Brassica napus;
<220> FEATURE:
<221> NAME/KEY: promoter
<222> LOCATION: (1)..(1790)
<223> OTHER INFORMATION: FAE1 promoter

<400> SEQUENCE: 20

| | |
|---|---|
| ggttgggcaa atctgacttc accaaagaaa caactcgagt cgttatccat ctcctcataa | 60 |
| ccatcgctcc actctttgcc ttcaccgttt tcggttcggt tctctacatc gcaacccggc | 120 |
| ccaaaccggt ttacctcgtt gagtactcat gctaccttcc accaacgcat tgtagatcaa | 180 |
| gtatctccaa ggtcatggat atcttttatc aagtaagaaa agctgatcct tctcggaacg | 240 |
| gcacgtgcga tgactcgtcg tggcttgact tcttgaggaa gattcaagaa cgttcaggtc | 300 |
| taggcgatga aactcacggg cccgaggggc tgcttcaggt ccctcccgg aagacttttg | 360 |
| cggcggcgcg tgaagagacg gagcaagtta tcattggtgc gctagaaaat ctattcaaga | 420 |
| acaccaacgt taaccctaaa gatataggta tacttgtggt gaactcaagc atgttttaatc | 480 |

```
caactccatc gctctccgcg atggtcgtta acactttcaa gctccgaagc aacgtaagaa      540
gctttaacct tggtggcatg ggttgtagtg ccggcgttat agccattgat ctagcaaagg      600
acttgttgca tgtccataaa aatacgtatg ctcttgtggt gagcacagag aacatcactt      660
ataacattta cgctggtgat aataggtcca tgatggtttc aaattgcttg ttccgtgttg      720
gtggggccgc tattttgctc tccaacaagc ctggagatcg tagacggtcc aagtacgagc      780
tagttcacac ggttcgaacg cataccggag ctgacgacaa gtcttttcgt tgcgtgcaac      840
aaggagacga tgagaacggc aaaatcggag tgagtttgtc caaggacata accgatgttg      900
ctggtcgaac ggttaagaaa aacatagcaa cgttgggtcc gttgattctt ccgttaagcg      960
agaaacttct ttttttcgtt accttcatgg caagaaact tttcaaagat aaaatcaaac       1020
attactacgt cccggatttc aaacttgcta ttgaccattt ttgtatacat gccggaggca      1080
gagccgtgat tgatgtgcta gagaagaacc tagccctagc accgatcgat gtagaggcat      1140
caagatcaac gttacataga tttggaaaca cttcatctag ctcaatatgg tatgagttgg      1200
catacataga agcaaaagga aggatgaaga aaggtaataa agtttggcag attgcttag       1260 ggtcaggctt taagtgtaac agtgcagttt gggtggctct aaacaatgtc aaagcttcga      1320
caaatagtcc ttgggaacac tgcatcgaca gatacccggt caaaattgat tctgattcag      1380
gtaagtcaga gactcgtgtc caaaacggtc ggtcctaata aacgatgttt gctctctttc      1440
gtttcttttt atttgttata ataatttgat ggctacgatg tttctcttgt ttgttatgaa      1500
taaagaatgc aatggtgttc tagtatttga ttgttttaca tgtatgtatc tcttatttac      1560
atgaaatttt taaacgccta aaaaaaaaaa cggaattccg atgacgtcca ttaacgtaaa      1620
gctcctttac cattacgtca taccaacct tttcaacctt tgcttctttc cgttaacggc       1680
gatcgtcgcc ggaaaagcct atcggcttac catagacgat cttcaccact tatactattc      1740
ctatctccaa cacaacctca taaccatcgc tccactcttt gccttcaccg                 1790
```

<210> SEQ ID NO 21
<211> LENGTH: 1210
<212> TYPE: DNA
<213> ORGANISM: Lunaria annua;
<220> FEATURE:
<221> NAME/KEY: promoter
<222> LOCATION: (1)..(1210)
<223> OTHER INFORMATION: FAE1 promoter

<400> SEQUENCE: 21

```
cgccggggag tttcagctta accggtaaaa ttggcctgta catatattta ccactgagta       60
aagacatcag ttaatgattt gttgttactc aattgggcta agtgtattat tatatgtgtt      120
gtatataata aaggtagaac gtaaatttac taagaatgtg ttttttccaat gtgattgctc     180 tttggcctct taggtttgaa tcctactcga gaagactaat tttaatttac tggcaaaaat      240
agaaatcaat ttataagtgt ttaaacaaat cgatggtata actgattagt gatcactctt      300
aggttttgat ccaactcgag tattgagtat tgaacgcttt ttttaaataa atcttgatt       360 tttaaattgg ttttttgagt aaaaaagttc ttaatatttt ctctttgttt taatgggttt     420
gttttgcatt ttataagctt aattttttcta atttaatatt ttatctatca tcgtccgtaa    480
agttttattt ggcacaaact tgtttttactt ttctaccttaa taatttggga actggttgag  540
tcaaagcgta ccggacaaat atgtttttata ttcttatttta agaattaaca ctcatctcat   600
aattagtcag aggctaggga gattcagcca atcaatgcta acaacaaaat tctcttaatg     660
```

-continued

| | | | |
|---|---|---|---|
| atctaacgat gctatttaat attcggatca gtattcttaa ataagaatat aaaactaatt | | | 720 |
| caatagttac agataaaaac ttatatagac tttttttattt ggaatataaa agtatcaata | | | 780 |
| tattatagac aatatttata acgttaaaaa tacaatatt atatttttta tatatttatt | | | 840 |
| tcaaattgaa aagcattact tctatcgaaa tgaattttag tatattaatt aatatttttt | | | 900 |
| taatcggact actttcctat tttggcacct ttcatctgac tactaattta tttcaatgtg | | | 960 |
| tatgcatgca tgagcatgag taatacacat gtctatataa atgcatgtaa aacgtaacgg | | | 1020 |
| accacaaaag tggatccata caaatacatc tcatcgcacc ctctccgaca caaaactgaa | | | 1080 |
| caatgacgtc tgtgaacgta aaactccttt accattacgt cataaccaac tttttcaacc | | | 1140 |
| tctgtttctt cccactgacg gggatcctcg ccggaaaagg ctctcgtctt accacaaacg | | | 1200 |
| atctccacca | | | 1210 |

<210> SEQ ID NO 22
<211> LENGTH: 1141
<212> TYPE: DNA
<213> ORGANISM: Artificial sequence
<220> FEATURE:
<221> NAME/KEY: promoter
<222> LOCATION: (1)..(1141)
<223> OTHER INFORMATION: consensus sequence of A.t., L.a., and B.n. FAE1
    promoters

<400> SEQUENCE: 22

| | | | |
|---|---|---|---|
| nnnnnnnnnn nnnnnnnnnn nnnnnnnnnn nnnnnnnnnn nnnnnnnnnn nnmsksrkwt | | | 60 |
| warmyckyrr wynnksrwwk gwykkkwybc anntsbryha rrwkdmktay bmtmtnkwgk | | | 120 |
| tgwrhrywrw rambdtvdhh yvtamnnawt tmcmmdkddk rtrwwwkknn natgwdddtk | | | 180 |
| yhmwnnngcb tvtwmvrykt drdwsbkrmn ygmbwwknws ydvtyywwvw ddmckrkvrr | | | 240 |
| wvrtrgrmrn ymvawbtahr rrynngwtba mayrrwtmnn nnnnakamck rakywgwnra | | | 300 |
| bvnstcttwk skttkvrtsc wanncragda nkdhkwwkws aamgvywnnn nnnnwtykka | | | 360 |
| rhbarwdwvv hsawkkwhan aahysrkkwt bykrktmvnn nngttmwkrm wawywkmdmd | | | 420 |
| wbgtynnnnn ggrtyygwtk nkkmwtyykw kannckwraw dhktcthnnt twwkmktywn | | | 480 |
| ncywksmtng kshrbaaavy twymwwwrry ahannnnwdy wwkactwyky bvcskwwnny | | | 540 |
| aawytksswn ytsryyrwkt nnswrwrsdt rsmgrannya rabhygykwn trwwbwshtw | | | 600 |
| bhbragaahy wmbmmmybakc hcmkawykak kyagaggsnn nnnnnnnnnn nnnnatcard | | | 660 |
| dyyaasrwya manakwyyyk baannayyth annwwgcwnn atdtrrtmwk nnnnnnagtw | | | 720 |
| knnnnnnakn asaaknyaaa avkaakkhwr wankwamrgw hadaaabttd krnngaytky | | | 780 |
| tttnnnntyr gvvtntaard gwannnnnnn nnnnnnngws dmwvttwaya nygtnnnnnn | | | 840 |
| nnnnayawwt nkwyyttddr wrbaytnnnn nnrmayygay addyayymsd tcdawmkwda | | | 900 |
| tkmnnattyn rgtawrtnnn nnnmtmktky ybhaawnnnn nngkmctaht wwvckatktt | | | 960 |
| kgcwmncttt crkyknnctw ytwmtttrtt wyaatrwktn natgsmtrcn atgwknnnyw | | | 1020 |
| tgwktrwtay rmatrwmkaw wkvmatgswn tnsyarwayk traykgwyyn acawrwrwgk | | | 1080 |
| atcymtdnaw wtacatswma thkynwhmck cnnnnnnnnt mmramamaaa ncdgarywnn | | | 1140 |
| n | | | 1141 |

<210> SEQ ID NO 23
<211> LENGTH: 1055
<212> TYPE: DNA
<213> ORGANISM: Artificial sequence
<220> FEATURE:

-continued

```
<221> NAME/KEY: promoter
<222> LOCATION: (1)..(1055)
<223> OTHER INFORMATION: consensus sequence of A.t. and L.a. FAE1
      promoters

<400> SEQUENCE: 23
actsakwaaa rmyakyagwt nntgrttkgt tgktwyycan ntgkrcyarr wgkmttayym      60
tatkwgttgw awrtwrwaam kktrkwmcst amnnawttmc tarkwrtgtr wwtktnnnat     120
gtrwwtgywm tnnngcstmt warryktrrw wcytamwyga swagnastrr ttytwrwkwm     180
ckrksarara trgrarymra wytawarrtg wtkamayaaw tmnnnnnnak aackrattwg     240
wraksnctct taggtttkra tccwaytcga gwatkkwktw ktsaamgmtw nnnnnnnttt     300
tkaamyaaar wmwwsatttw waaawtsrkt wtyygrktam nnnngttcwt rmwawtwkmw     360
mktkgtttwn nnggrtytgw ttkkmatttt akanncttaa wkwktctmnn ttaakattyw     420
atcywksmtn gtsyryaaar ytwyawwtrr yayannnntk tttwkactwtt ykrccttann    480 taawytkssa nctsrttrwk tncwragskt asmgrayara ywtgykwnta waywcwtwyy     540
yragaawtam ymmtsatcyc ataattagtc agaggstakg nnnnnnnnnc caatcarwkc     600
taasaacama nattcyctya annatytwan natgcwnatk taatmwtnnn nnnagtwtnn     660
nnnnakmasa atwyaaaamt aatkyartan ttamagayar aaayttrtan ngacttttt     720 nnttggmrtn taaargwann nnnnnnnnnn ngacwawrtt tatancgtnn nnnnnnnay     780 atttntattt twwrtrkann nnnnnnaaay ygaaawknnt tmcwtckawm kawatgaatt     840
tnagtatatn nnnnnatatt tytkyaatng kactayttts ctattttggc amctttcaky    900
kgactactam tttattwcaa tgtgtatgsa tgcatgagyw tgagtantac acatgtctaw    960
atrmatgcwt ngyaaaacgt aacggaccac aaaagwggat ccatrcaaat acatctcatm   1020
gcwycctcnn nnnnntccg acacaaancw garca                              1055
```

REGULATION OF EMBRYONIC TRANSCRIPTION IN PLANTS

This application claims benefit of provisional application No. 60/147,133, filed Aug. 4, 1999.

FIELD OF THE INVENTION

The invention is in the field of nucleic acid sequences capable of regulating transcription, particularly sequences that may promote transcription during embryogenesis in plants.

BACKGROUND OF THE INVENTION

Most of the information about seed-specific gene expression comes from studies of genes encoding seed storage proteins like napin, a major protein in the seeds of *Brassica napus*, or conglycinin of soybean. Upstream DNA sequences directing strong embryo-specific expression of these storage proteins have been used successfully in transgenic plants to manipulate seed lipid composition and accumulation (Voelker et al., 1996). However, expression of storage protein genes begins fairly late in embryogenesis. Thus, promoters of seed storage protein genes may not be ideal for all seed-specific applications. For example, storage oil accumulation commences significantly before the highest level of expression of either napin (Stalberg et al., 1996) or conglycinin (Chen et al., 1988) is achieved. It is, therefore of interest to identify other promoters which may modulate expression of genes in developing plant embryos.

A variety of transcriptional regulatory regions that may be active during plant embryogenesis are known, as disclosed for example in: U.S. Pat. No. 5,792,922 issued Aug. 11, 1998 to Moloney; U.S. Pat. No. 5,623,067 issued Apr. 22, 1997 to Vandkerckhove et al.; International Patent Publication WO9845461 published Oct. 15, 1998. There remains a need for alternative transcriptional regulatory regions.

FATTY ACID ELONGATION1 (FAE1) genes encode condensing enzymes involved in plant very long chain fatty acid biosynthesis. The FAE1 condensing enzyme is thought to be localized in the endoplasmic reticulum where it catalyzes the sequential elongation of C18 fatty acyl chains to C22 in length (Kunst et al., 1992). FAE1 genes have been cloned and described recently by James et al. (1995), International Patent Publication WO 96/13582.

SUMMARY OF THE INVENTION

In one aspect, the invention provides transcriptional regulatory regions derived from FAE1 genes. The transcriptional regulatory regions of the invention may be useful in promoting early seed-specific transcription of heterologous sequences to which they are operably linked. The transcriptional regulatory regions of the invention may be used in a wide variety of plants, including Brassica sp., Arabidopsis and other plant species. DNA constructs comprising the transcriptional regulatory sequences of the invention may be active during fatty acid or lipid biosynthesis in the plant embryo. Certain embodiments of the constructs of the invention may be used in transgenic plants to promote expression of heterologous sequences in developing seeds. In various embodiments, the constructs of the invention may be used to mediate gene expression that affects seed lipid metabolism, or seed protein composition or seed carbohydrate composition, or seed development. In alternative embodiments, the transcriptional regulatory regions of the invention may also be useful for the production of modified seeds containing novel recombinant proteins which have pharmaceutical, industrial or nutritional value.

BRIEF DESCRIPTION OF THE DRAWINGS

FIG. 1 shows a 934 bp DNA sequence (SEQ ID NO:16) comprising *Arabidopsis thaliana* FAE1 transcription regulatory sequence.

FIGS. 2A–2B show a 1588 bp DNA sequence comprising the *Brassica napus* FAE1 transcription regulatory sequence.

FIGS. 3A–3B show a 1069 bp DNA sequence comprising the *Lunaria annua* FAE1 transcription regulatory sequence.

FIGS. 4A–4C show an alignment of the *Arabidopsis thaliana* (*A.t.*), *Lunaria annua* (*L.a.*) and *Brassica napus* (*B.n.*) transcription regulatory sequences. Asterisks below the sequences indicate identical nucleotides in each of the three sequences. A number of putative cis-acting sequence motifs are identified in the *A. thaliana* sequence: an EM1 ABA box at –44 bp to –36 bp having the sequence ACATCTCAT, for which the published consensus sequence is ACGTGTCAT (Rowley, D. L. and Herman, E. M. (1997), Biochimica et Biophysica Acta 1345:1–4); an A-300 box at –51 bp to –46 bp having the sequence TGCAAT, for which the published consensus sequence is TG(T/AC) AAA (G/T) (Morton et al. (1994) in Seed Development and Germination (Kigel, J. and Gallili, G., eds.) pp. 103–138, Marcel Dekker. New York); G-box 1 at –105 to –100 bp having the sequence CACATG, for which is the consensus sequence is CACCTG, and G-box 2 at –164 to –159 bp having the sequence CAACTT, for which the consensus sequence is CAACTG (Kawogoe, Y. and Murai, N. (1992) Plant J. 2:927–936; CE1 element at –226 to –218 bp having the sequence TTCCATCGA, for which the consensus sequence is TGCCACCGG, and CE3 element at 381 bp to –369 bp having the sequence ACACATTCCCTC, for which the consensus sequence is ACGCGTGTCCTC (Shen et al., (1996) Plant Cell 8:1107–1119). Not highlighted is a putative RY repeat motif at –53 bp to –47 bp having the sequence CATGCAA, for which the consensus sequence is CATGCAT (Dickinson et al. (1988) Nucleic Acid Res. 16:371; Lelievre et al. (1992) Plant Physiol. 98:387–391). Also shown, as Con. 4, is a consensus sequence, wherein R=G or A, Y=T/U or C, M=A or C, K=G or T/U, S=G or C, W=A or T/U, B=G or C or T/U, D=A or G or T/U, H=A or C or T/U, V=A or G or C and N=A or G or C or T/U.

FIG. 5 shows an alignment of the *Arabidopsis thaliana* (*A.t.*) and *Lunaria annua* (*L.a.*) transcription regulatory sequences. Asterisks below the sequences indicate identical nucleotides in each of the two sequences. The base at position –400 in the *A.t.* sequence is highlighted. The alignment of sequences in both FIG. 4 and FIG. 5 was accomplished using the CLUSTALW program (version 1.74) for multiple sequence alignments, using a gap open penalty of 15, a gap extension penalty of 6.66 and an IUB DNA weight matrix. Also shown, as Con. 5, is a consensus sequence (SEQ ID NO:23), wherein R=G or A, Y=T/U or C, M=A or C, K=G or T/U, S=G or C, W=A or T/U, B=G or C or T/U, D=A or G or T/U, H=A or C or T/U, V=A or G or C and N=A or G or C or T/U.

FIGS. 7A–7B show an alignment of the *Brassica napus* (*B.n.*) and *Lunaria annua* (*L.a.*) FAE1 transcription regulatory sequences. Asterisks below the sequences indicate identical nucleotides in each of the two sequences.

FIGS. 8A–8B show an alignment of the *Brassica napus* (*B.n.*) and *Arabidopsis thaliana* (*A.t.*) FAE1 transcription regulatory sequences. Asterisks below the sequences indicate identical nucleotides in each of the two sequences.

DETAILED DESCRIPTION OF THE INVENTION

Figure 6A:
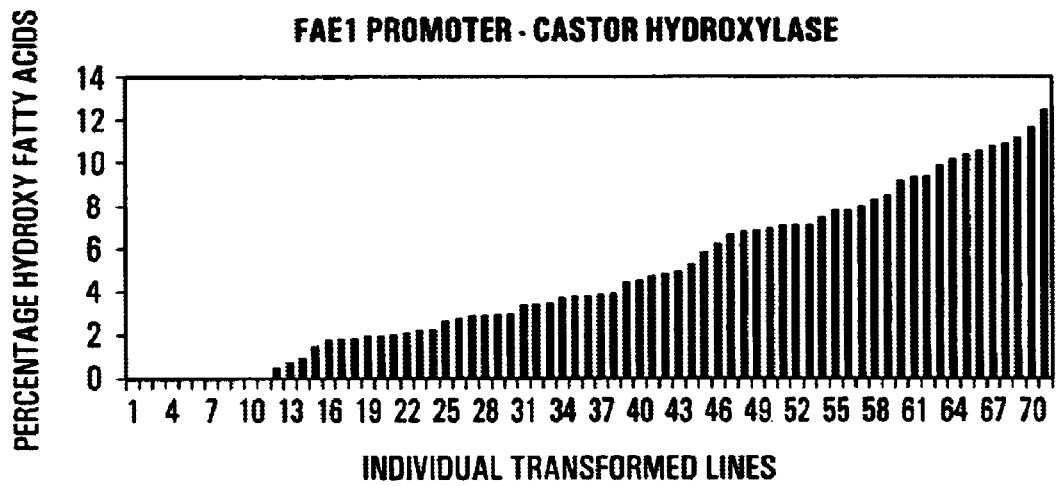
FIG. 6 includes two bar graphs illustrating hydroxy fatty acid content of A) FAE1–FAH12 and B) napin-FAH12 transgenic seeds, expressed as percentage of total seed fatty acids.

The recombinant nucleic acid molecules of the invention may comprise a heterologous promoter sequence operably linked to a nucleic acid sequence, wherein the promoter sequence comprises a transcriptional regulatory region capable of mediating seed-specific expression in Arabidopsis. The transcriptional regulatory region may be obtainable from a plant FAE1 gene. Alternatively, The transcriptional regulatory region may hybridize under stringent conditions to a 5' region of the plant FAE1 gene. In further alternative embodiments, The transcriptional regulatory region may be at least 70% identical when optimally aligned to the 5' region of the plant FAE1 gene.

In alternative embodiments, the invention provides isolated nucleic acids comprising the transcriptional regulatory regions of the invention. By isolated, it is meant that the isolated substance has been substantially separated or purified away from other biological components with which it would otherwise be associated, for example in vivo. The term "isolated" therefore includes substances purified by standard purification methods, as well as substances prepred by recombinant expression in a host, as well as chemically synthesized substances.

In the context of the present invention, "transcriptional regulatory region" means a nucleotide sequence capable of mediating or modulating transcription of a nucleotide sequence of interest, when the transcriptional regulatory region is operably linked to the sequence of interest. Conversely, a transcriptional regulatory region and a sequence of interest are "operably linked" when the sequences are functionally connected so as to permit transcription of the sequence of interest to be mediated or modulated by the transcriptional regulatory region. In some embodiments, to be operably linked, a transcriptional regulatory region may be located on the same strand as the sequence of interest. The transcriptional regulatory region may in some embodiments be located 5' of the sequence of interest. In such embodiments, the transcriptional regulatory region may be directly 5' of the sequence of interest or there may be intervening sequences between these regions. The operable linkage of the transcriptional regulatory region and the sequence of interest may require appropriate molecules (such as transgenic activator proteins) to be bound to the transcriptional regulatory region, the invention therefore encompasses embodiments in which such molecules are provided, either in vitro or in vivo.

The term "recombinant" means that something has been recombined, so that when made in reference to a nucleic acid molecule the term refers to a molecule that is comprised of nucleic acid sequences that are joined together by means of molecular biological techniques. The term "recombinant" when made in reference to a protein or a polypeptide refers to a protein molecule which is expressed using a recombinant nucleic acid molecule. The term "heterologous" when made in reference to a nucleic acid sequence refers to a nucleotide sequence which is ligated to, or is manipulated to become ligated to, a nucleic acid sequence to which it is not ligated in nature, or to which it is ligated at a different location in nature. The term "heterologous" therefore indicates that the nucleic acid molecule has been manipulated using genetic engineering, i.e. by human intervention.

Sequences may be derived or obtainable from plant FAE1 genes by deduction and synthesis based upon the wild-type FAE1 gene sequences. Derived sequences may be identified in different organisms, for example by isolation using as probes the nucleic acid sequences of the invention. Alternative transcriptional regulatory regions may be derived through mutagenesis or substitution of wild-type sequences, such as the sequence disclosed herein. Derived nucleic acids of the invention may be obtained by chemical synthesis, isolation, or cloning from genomic DNAs using techniques known in the art, such as the Polymerase Chain Reaction (PCR). Consensus sequences, such as those illustrated in FIGS. 4 and 5 are alternative embodiments of the nucleic acids of the invention, derived from the disclose wild-type FAE1 gene sequences. Nucleic acids of the present invention may be used to design alternative primers (probes) suitable for use as PCR primers to amplify particular regions of an FAE1 gene. Such PCR primers may for example comprise a sequence of 15–20 consecutive nucleotides of the sequences of the invention. To enhance amplification specificity, primers of 20–30 nucleotides in length may also be used. Methods and conditions for PCR amplification are described in Innis et al. (1990); Sambrook et al. (1989); and Ausubel et al. (1995). As used herein, the term "probe" when made in reference to an oligonucleotide refers to an oligonucleotide which is capable of hybridizing to another oligonucleotide of interest. A probe may be single-stranded or double-stranded. Probes are, for example, useful in the detection, identification, amplification and isolation of particular gene sequences. Oligonucleotide probes may be labelled with a "reporter molecule," so that the probe is detectable using a detection system, such as enzymatic, fluorescent, radioactive or luminescent detection systems.

Derived nucleic acids of the invention may also be identified by hybridization, such as Southern or Northern analysis. Southern analysis is a method by which the presence of DNA sequences in a target nucleic acid mixture are identified by hybridization to a labeled probe, comprising an oligonucleotide or DNA fragment of a nucleic acid of the invention. Probes for Southern analysis may for example be at least 15 nucleotides in length. Southern analysis typically involves electrophoretic separation of DNA digests on agarose gels, denaturation of the DNA after electroporetic separation, and transfer of the DNA to nitrocellulose, nylon, or another suitable membrane support for analysis with a radiolabeled, biotinylated, or enzyme-labeled probe as described in Sambrook et al. (1989). Similarly, Northern analysis may be used to identify RNAs that hybridize to a known probe such as an oligonucleotide. DNA fragment, cDNA or fragment thereof, or RNA fragment of a nucleic acid of the invention or a known FAE1 sequence. The probe may be labeled with a radioisotope such as $^{32}$P, by biotinylation or with an enzyme. The RNA to be analyzed may be electrophoretically separated on an agarose or polyacrylamide gel, transferred to nitrocellulose, nylon, or other suitable membrane, and hybridized with the probe, using standard techniques well known in the art such as described in Sambrook et al. (1989).

In alternative embodiments, a transcriptional regulatory region of the invention may be at least 70% identical when optimally aligned to the 5' region of a plant FAE1 gene, such as the Arabidopsis FAE1 gene. In alternative embodiments, the degree of identity may be between 50% and 100%, such as 60%, 80%, 90%, 95% or 99%. When a position in the compared sequence is occupied by the same nucleotide or amino acid, following optimal alignment of the sequences, the molecules are considered to have identity at that position. The degree of identity between sequences is a function of the number of matching positions shared by the sequences. In terms of percentage, identity is the sum of identical positions, divided by the total length over which the sequences are aligned, multiplied by 100.

Various aspects of the present invention encompasses nucleic acid or amino acid sequences that are homologous to other sequences. As the term is used herein, an amino acid or nucleic acid sequence is "homologous" to another sequence if the two sequences are substantially identical and the functional activity of the sequences is conserved (for example, both sequences function as or encode a FAE1 enzyme: as used herein, the term "homologous" does not infer evolutionary relatedness). Nucleic acid sequences may also be homologous if they encode substantially identical amino acid sequences, even if the nucleic acid sequences are not themselves substantially identical, a circumstance that may for example arise as a result of the degeneracy of the genetic code.

Two amino acid or nucleic acid sequences are considered substantially identical if, when optimally aligned (with gaps permitted), they share at least about 50% sequence similarity or identity, or if the sequences shared defined functional motifs. In alternative embodiments, sequence similarity in optimally aligned substantially identical sequences may be at least 60%, 70%, 80%, 90% or 95%. As used herein, a given percentage of homology between sequences denotes the degree of sequence identity in optimally aligned sequences.

Optimal alignment of sequences for comparisons of similarity may be automated using a variety of algorithms, such as the local homology algorithm of Smith and Waterman (1981) *Adv. Appl. Math* 2: 482, the homology alignment algorithm of Needleman and Wunsch (1970) *J. Mol. Biol.* 48:443, the search for similarity method of Pearson and Lipman (1988) *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence similarity may also be determined using the BLAST algorithm, described in Altschul et al. (1990), *J. Mol. Biol.* 215:403–10 (using the published default settings). Software and instructions for performing BLAST analysis may be available through the National Center for Biotechnology Information in the United States (including the programs BLASTP, BLASTN, BLASTX, TBLASTN and TBLASTX that may be available through the internet at the NCBI website. The BLAST algorithm involves first identifying high scoring sequence pairs (HSPs) by identifying short words of length W in the query sequence that either match or satisfy some positive-valued threshold score T when aligned with a word of the same length in a database (reference) sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defualts a word length (W) of 11, the BLOSUM62 scoring matrix (Henikoff and Henikoff (1992) *Porc. Natl. Acad. Sci. USA* 89: 10915–10919), a gap existence cost of 11, a per residue gap cost of 1, a lambda ratio of 0.85, alignments (B) of 50, expectation (E) of 10, M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probabability in a comparison of the test sequences is less than about 1, preferably less than about 0.1, more preferably less than about 0.01, and most preferably less than about 0.001. In the PSI-BLAST implementation of the BLAST algorithm, an expect value for inclusion in PSI-BLAST iteration may be 0.001 (Altschul et al. (1997), *Nucleic Acids Res.* 25:3389–3402). Searching parameters may be varied to obtain potentially homologous sequences from database searches.

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65EC, and washing in 0.2× SSC/0.1% SDS at 42EC (see Ausubel, et al. (eds.) 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65EC, and washing 0.1× SSC/0.1% SDS at 68EC (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsvier, N.Y.). Generally, stringent conditions are selected to be about 5EC lower than the thermal melting point for the specific sequence at a defined ionic strength and pH.

A FAE1 promoter is any naturally occurring transcriptional regulatory region that mediates or modulates the expression of a plant FAE1 condensing enzyme. Plant FAE1 condensing enzymes are proteins that are homologous to known FAE1 condensing enzymes, such as those cloned and described in International Patent Publication WO 96/13582.

Heterologous DNA sequences may for example be introduced into a host cell by transformation. Such heterologous molecules may include sequences derived from the host cell species, which have been isolated and reintroduced into cells of the host species. Heterologous nucleic acid sequences may become integrated into a host cell genome, either as a result of the original transformation of the host cells, or as the result of subsequent recombination events. Transformation techniques that may be employed include plant cell membrane disrutpion by electroporation, microinjected and polyethylene glycol based transformation (such as are disclosed in Paskowski et al. *EMBO J.* 3:2717 (1984); Fromm et al., *Proc. Natl. Acad. Sci USA* 82:5824 (1985); Rogers et al., *Methods of Enzymol.* 118:627 (1986); and in U.S. Pat. Nos. 4,684,611; 4,801,540; 4,743,548 and 5,231,019), biolistic transformation such as DNA particle bombardment (for example as disclosed in Klein et al., *Nature* 327: 70

(1987); Gordon-Kamm, et al. "The Plant Cell" 2:603 (1990); and in U.S. Pat. Nos. 4,945,050; 5,015,580; 5,149,655 and 5,466,587); Agrobacterium-mediated transformation methods (such as those disclosed in Horsch et al. *Science* 233: 496(1984); Fraley et al., *Proc. Nat'l. Acad. Sci. USA* 80:4803 (1983); and U.S. Pat. Nos. 4,940,838 and 5,464, 763).

Standard methods are available for the preparation of constructs for use in identifying and characterizing transcriptional regulatory regions useful in various embodiments of the invention. General techniques may for example be performed by procedures generally described by Ausubel F M, Brent R. Kingston R E. Moore D D. Seidman J G. Smith J A. Stuhl K. (1995) Current Protocols in Molecular Biology, Vols. 1, 2 and 3. Alternative equivalent methods or variations thereof may be used in accordance with the general knowledge of those skilled in this art and the functional requirements of the present invention.

In some aspects of the invention, transformed plant cells may be cultured to regenerate whole plants having a transformed genotype and displaying a desired phenotype, as for example modified by the expression of a heterologous protein mediated by a transcriptional regulatory region of the invention. A variety of plant culture techniques may be used to regenerate whole plants, such as are described in Gamborg and Phillips. "Plant Cell, Tissue and Organ Culture, Fundamental Methods", Springer Berlin, 1995); Evans et al. "Protoplasts Isolation and Culture", Handbook of Plant Cell Culture, Macmillian Publishing Company, New York, 1983; or Binding, "Regeneration of Plants, Plant Protoplasts", CRC Press, Boca Raton, 1985; or in Klee et al., *Ann. Rev. of Plant Phys.* 38:467 (1987). A cell, tissue, organ, or organism into which has been introduced a foreign nucleic acid, is considered "transformed", "transfected", or "transgenic". A transgenic or transformed cell or organism also includes progeny of the cell or organism and program produced from a breeding program employing a transgenic plant as a parent in a cross and exhibiting an altered phenotype resulting from the presence of a recombinant nucleic acid construct. A transgenic plant is therefore a plant that has been transformed with a heterologous nucleic acid, or the progeny of such a plant that includes the transgene. The invention provides vectors, such as vectors for transforming plants or plant cells. The term "vector" in reference to nucleic acid molecule generally refers to a molecule that may be used to transform a nucleic acid segment(s) from one cell to another. One of skill will recognize that after the nucleic acid is stably incorporated in transgenic plants and confirmed to be operable, it can be introduced into other plants by sexual crossing. Any of a number of standard breeding techniques may be used, depending upon the species to be crossed.

In various embodiments, the invention comprises plants transformed with the nucleic acids of the invention. In some embodiments, such plants will exhibit altered fatty acid content in one or more tissues. These aspects of the invention relate to all higher plants, including monocots and dicots, such as species from the genera Fragaria, Lotus, Medicago, Onobrychis, Triforium, Trigonelia, Wgna, Citrus, Linum, Gerantum, Manihor, Caucus, Arabidopsis, Brassica, Raphanus, Sinapis, Atropa, Capsicum, Hyoscyamus, Lycopersicon, Nicotiana, Solanum, Petunia, Digitulis, Majorana, Cichorium, Helianthus, Lactuca, Bromus Asparagus, Antirrhinum, Heterocatlis, Nemesia, Pelargonium, Panicum, Penniserum, Ranunculus, Senecio, Salpiglossis, Cucarnis, Browallia, Glycine, Lolium, Zea, Triticum, Sorghum, and Datura. Such plants may include maize, wheat, rice, barley, soybean, beans, rapeseed, canola, alfalfa, flax, sunflower, cotton, clover, lettuce, tomato cucurbits, potato carrot, radish, pea lentils, cabbage, broccoli, brussel sprouts, peppers, apple, pear, peach, apricot, carnations and roses. More specifically, in alternative emboidments, plants for which the invention may be used in modifying fatty acid content include oil crops of the Cruciferae family: canola, rapeseed (Brassica spp.), crambe (Crambe spp.), honesty (Lunaria spp.) lesquerella (Lesquerela spp.), and others: the Composirae family; sunflower (Helianthus spp.), safflower (Carthamus spp.), niger (Guizotia spp.) and others; the Palmae family; palm (Elaeis spp.), coconut (Cocos spp.) and others; the Leguminosae family; peanut (Arachis spp.), soybean (Glycine spp.) and others; and plants of other families such as maize (Zea spp.), cotton (Gossvptun sp.), jojoba (Simonasia sp.), flax (linum sp.), sesame (Sesamum spp.), castor bean (Ricinus spp.), olive (Olea spp.), poppy (Papaver spp.), spurge (Euphorbia, spp.), meadowfoam (Limnanthes spp.), mustard (Sinapis spp.) and cuphea (Cuphea spp.).

Nucleic acids of the invention may also be used as a plant breeding tool, as molecular markers to aid in plant breeding programs. Such techniques would include using the gene itself as a molecular probe or using the DNA sequence to design PCR primers to use PCR based screening techniques in plant breeding programs.

Deletion or insertion constructs may be useful for domain mapping to determine the functional domains or motifs of a transcriptional regulatory region derived from a FAE1 gene. An aspect of the invention is the construction and testing of such constructs, as described below for the 5' deletion construct of the *A. thaliana* FAE1 5' region. One aspect of the invention comprises transcriptional regulatory regions that are derived from functionally important regions of a FAE1 promoter. As outlined above, the functionally important regions of a FAE1 promoter may be determined through routine assays. Alternatively, randomly selected portions of a FAE1 promoter may be selected for use in routine assays to determine whether the selected region is capable of functioning as a transcriptional regulatory region in the context of the present invention. In various embodiments, regions of the *Arabidopsis thaliana, Brassica napus* or *Lunaria annua* promoters may be used. For example, the following motifs in the *A.t.* FAE1 promoter may be used alone or in combination in novel transcriptional regulatory regions (see FIG. 4): the CE-like elements (CE1 and CE3), the RY repeat motif, the G-boxes (G-box1 and G-box2), the A-300 box, the EM1 ABA box, or the CTATTTTG element. Constructs of the invention comprising such motifs, deletions or insertions may be assayed for activity as transcriptional regulatory regions of the invention by testing for storing seed-specific activity providing expression of a sequence of interest (such as a reporter sequence) before the torpedo stage and persisting throughout embryo development in accordance with standard testing methods that may be adapted from the methods disclosed herein.

Alternative embodiments of the transcriptional regulatory regions of the invention may be identified using information available through NCB1 databases at http://www.nebi.nih.gov.

In various embodiments, transcriptional regulatory regions derived from plant FAE1 genes are shown to be capable of directing expression of desired genes at an early stage of development in a seed-specific manner in disparate plant species. In particular embodiments, the transcriptional regulatory regions of the invention may be used in a wide variety of dicotyledonous plants for modification of the seed phenotype. For example, new seed phenotypes may include:

(1) altered seed fatty acid composition or seed oil composition and accumulation
(2) altered seed protein or carbohydrate composition or accumulation
(3) enhanced production of desirable endogenous seed products
(4) suppression of production of undesirable gene products using antisense, co-suppression or ribozyme technologies
(5) production of novel recombinant proteins for pharmaceutical, industrial or nutritional purposes Isolation of a seed-specific promoter from *A. thaliana*

Using the sequence information of the *A. thaliana* genome sequencing project, synthetic oligonucleotide primers were designed to amplify the FAE1 5' untranslated region, to isolate it by PCR. As shown in FIG. 1, the upstream primer 5'-CTAGTAGATTGGTTGGTTGGTTTCC-3' (AtproFW) (SEQ ID NO:3) in combination with the downstream primer 5'-TGCTCTGTTTGTGTCGGAAAATAATGG-3' (AtproRV) (SEQ ID NO:4) were used, and resulted in the synthesis of a fragment of the correct size (934 bp). The amplified product was subcloned in the HincII site of the plasmid pT7T3-18U (Pharmacia) to produce plasmid pT7T3-18U/proFAE900, followed by complete sequence determination of both strands to verify the fragment identity. A BLAST search of the *A. thaliana* Database identified a single BAC clone T4L20 (GenBank ATF10M6) 125,179 bp long, which contains the complete FAE1 gene.

Functional analysis of the FAE1 5' upstream region

5' upstream fragments of the FAE1 gene were shown to confer seed-specific and temporally regulated gene expression in plants. A translational fusion was made between the FAE1 5' region and the coding region of the reporter gene β-glucuronidase (GUS). The chimeric gene (pFAE900-GUS or pFAE400-GUS) was transferred into Arabidopsis and tobacco and GUS activity was monitored in various tissue of transgenic plants.

Construction of the vectors pFAE900-GUS and PFAE400-GUS, and transformation of Arabidopsis and tobacco, was as follows. The insert was cleaved out of pT7T3-18U vector with HindIII and XbaI and directionally subcloned into the corresponding sites of the binary Ti plasmid pB1101 (Clontech), which contains a promoterless GUS gene (Jefferson et al. 1987), to obtain the vector pFAE900-GUS. Another construct, pFAE400-GUS, containing only 393 bp of the 5' FAE1 region directly upstream of the ATG initiation codon (SEQ ID NO:15) fused to the GUS coding sequence was also generated. For that, the pT7T3-18U/proFAE900 vector was digested with BglII and PstI, the sticky ends were filled in using T4 DNA polymerase, followed by re-ligation to obtain pT7T3-18U/proFAE400. The 393 bp 5' FAE1 upstream fragment was then excised with HindIII and XbaI and cloned into the binary vector pB1101 to obtain the plasmid pFAE400-GUS. The pFAE400-GUS and pFAE900-GUS fusion constructs in pBI101 were introduced into *Agrobacterium tumefaciens* strain GV3101 (Koncz and Schell, 1986) by heat-shock and selected for resistance to kanamycin (50 μg/ml). *A. thaliana* (L.) Heynh. ecotype Columbia was transformed with the pFAE400-GUS and pFAE900-GUS constructs using floral dip method (Clough and Bent, 1998). Screening for transformed seed was done on 50 μg/mL kanamycin as described previously (Katavie et al., 1994). Approximately 100 transgenic lines were generated for each construct.

For transformation of tobacco, *A. tumefaciens* harbouring the pFAE900-GUS construct was co-cultivated with leaf pieces of *Vicotiana tabacum* SR1 and transformants were selected with kanamycin (100 μg/mL) on solid medium (Lee and Douglas, 1996).

Histochemical localization of GUS activity and analysis of transgenic plants was as follows. Tissue sections were placed in 100 mM NaPO$_4$ (pH7) and 1 mM spermidine for 15 min, then incubated at 37° C. in 0.5 K$_3$[Fe(CN)$_6$], 0.01% Triton X-100, 1 mM EDTA, 10 mM β-mercaptoethanol, 5-bromo-4-chloro-3-indolyl-β-D-glucuronide in 100 mM NaPO$_4$ (pH7), until a blue color appeared (after approximately 1 hr). Following incubation with the substrate, chlorophyll was removed from the sections using a graded ethanol series.

Using this assay, five independent transgenic Arabidopsis lines were examined for the embryo-specific expression of the GUS gene. In addition, leaf, steam and siliques were histochemically stained for β-glucuronidase activity. The results indicate that the reporter gene fused to the transcriptional regulatory region of the invention is not expressed in vegetative tissues, whereas it is highly expressed in developing seeds (embryos). Both the 934 bp and the 393 bp transcriptional regulatory regions derived from the *A.t.* FAE1 gene caused the appearance of GUS activity by the torpedo stage embryo (6 days after flowering). GUS activity in all five lines persisted throughout subsequent embryo development.

Leaves, stems, pods and seeds of three regenerated tobacco lines transformed with the pFAE900-GUS construct were also assayed for β-glucuronidase activity. The results obtained indicate that the 934 bp FAE1 promoter fragment contains sufficient information to direct seed-specific expression of a reporter gene in transgenic tobacco. Thus the transcriptional regulatory regions of the invention may be used for seed-specific expression of foreign genes in transgenic plants.

Figure 6B:
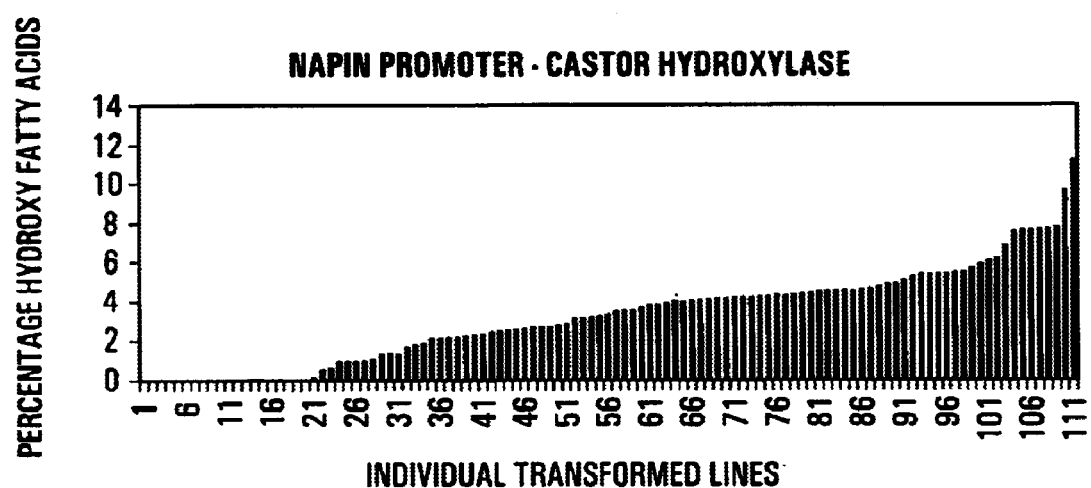

The in vivo activity of a FAE1 promoter of the invention was compared to the activity of the napin promoter by expressing the castor bean hydroxylase gene FAH12 (Broun and Somerville, 1997) behind either the FAE1-promoter (a transcriptional regulatory region of approximately 1 kb) or the napin promoter in an Arabidopsis fad2/fae1 double mutant. This mutant accumulates as a proportion of fatty acids about 85% of the 18:1 acyl group, which is the substrate for the hydroxylase. The levels of hydroxylated fatty acids accumulating in a large number of independent transgenic lines were used to estimate the relative strength of each promoter. As shown in FIG. 6, the two populations of transgenic plants accumulated levels of hydroxylated fatty acids, ranging from 0.2% to about 11–12% of total fatty acids, with the levels being on average slightly higher in FAE1-FAH12 lines. Similarly, the best FAE1-FAH12 plant accumulated just over 12% of hydroxylated fatty acids (w/w of total FAs), whereas the best napin-FAH12 plant produced 10.8% of hydroxylated fatty acids (w/w of total FAs). These results indicate that the FAE1 promoter is highly active in transgenic Arabidopsis and that its in vivo activity may be superior to napin in Arabidopsis seeds.

Sequence elements or motifs that confer both tissue specificity and developmental regulation of transcription reside within 393 bp of the AUG translation initiation codon in the *A.t.* FAE1 gene. The seed-specific expression conferred by the transcriptional regulatory regions of the invention is independent of the native terminator of the FAE1 gene 3' end. For example, in the exemplified constructs disclosed herein, a terminator derived from the Agrobacterium nopaline synthase gene was used.

*Lunaria annua* and *Brassica napus* FAE1 5' regulatory regions

Two sequences originating from B. napus and L. annua were isolated and characterized to demonstrate that regulatory regions conferring seed-specific transcription early in embryo development can also be found upstream of other plant FAE1 genes. Sequences were cloned using the technique of polymerase chain reaction (PCR) walking on uncloned plant genomic DNA (Devic et al., 1997). Approximately 5 µg of genomic DNA from 1 g of fresh tissue was used for the construction of 5 different libraries by digesting DNA with a series of enzymes that produce blunt end fragments to which special adaptors are ligated. The adaptor molecules consist of a long upper strand, which contains successive sequences common to the adaptor primers. AP1 and AP2, annealed at its 3' end to a shorter strand lacking the AP1 sequence. However, this short strand possesses an amine group at its 3' end to prevent filling in by the DNA polymerases during the first PCR amplification step and generation of the AP1 binding site. This suppression PCR effect prevents exponential amplification of molecules containing the adaptor at each end, and the adaptor primer binding sites are only produced when a strand complementary to the upper strand of the adaptor is synthesized by extension from a gene specific primer. The first PCR reaction is performed using an adaptor primer AP1 and a gene specific primer. An aliquot of the first PCR product is used a template in a second PCR amplification using the nested gene specific primer and AP2.

In order to isolate the regulatory regions upstream of the B. napus FAE1 coding sequence, genomic DNA was prepared from developing leaves and digested with 5 blunt-end cutting restriction enzymes (DraI, EcoRV, HpII, PvuII and ScaI) to generate a series of DNA libraries. After ligation of adapter molecules, individual libraries were used as templates in a two step PCR. In the first PCr amplification using the AP1 primer 5'-GGATCCTAATACGACTCACTATAGGGC-3' (SEQ ID NO:5) and the FAE1 gene specific primer 5'-AAAGAGTGGAGCGATGGTTATGAGG-3' (SEQ ID NO:6) (Bnwalk1), multiple DNA fragments were amplified from all five library templates. After a second round of PCR, using the AP2 primer 5'-CTATAGGGCTCGAGCGGC-3' (SEQ ID NO:7) and the nested FAE1 specific primer 5'-CGGAAAGAAGCAAAGGTTGAAAGG-3' (SEQ ID NO:8) (Bnwalk2), the longest single fragment of 1.6 kb was obtained from the HpaI library template. This fragment was inserted into the pCR2.1 plasmid (Invitrogen) and sequenced. The sequence is shown in FIG. 2.

For the PCR walking experiment to isolate the L. annua 5' regulatory region, in addition to the stranded AP1 and AP2 primers, the following FAE1 specific primers were used: 5'-GATCGTTTGTGGTAAGACGAGAGC-3' (SEQ ID NO:9) (Lawalk1) and 5'-GTCAGTGGGAAGAAACAGAGGTTG-3' (SEQ ID NO:10) (Lawalk2). In the first PCR reaction, the DraI, EcoRV, PvuII, ScaI and SpsI library templates were used. In a second PCR amplification the longest single fragment 1.1 kb in length was synthesized using the EcoRV library template. This fragment was inserted into the HincII site of the pT7T3-18U vector (Promega), sequenced on both strands and analyzed (FIG. 3).

Using the sequence data obtained for the 5' regulatory regions generated by PCR walking, specific primers were generated for the amplification of the L. annua and B. napus FAE1 promoter fragments. For the PCR-amplification of B. napus promoter fragment the upstream primer was 5'-CTGACTTCACCAAAGAAACAACTCG-3' (SEQ ID NO:11) (BnproFW) in combination with the downstream primer 5'-CGGAATTCCGTTTTTTTTTTAGGCG-3' (SEQ ID NO:12) (BnproRV). The synthesized fragment was ligated into SmaI site of pGEM-72f (Promega), then excised with XbaI/BamHI and cloned into the equivalent sites of the pBI101 binary vector (Clontech). L. annua 5' regulatory region was amplified using the 5'-CAGCTTAACCGGTAAAATTGGCC-3' (SEQ ID NO:13) (LaproFW) upstream primer together with the 5'-TGTTCAGTTTTGTGTCGGAGAGG-3' (SEQ ID NO:14) (LaproRV) downstream primer and inserted into the HincII site of pT7T3-18U (Promega) plasmid. In order to clone the L. annua promoter fragment into the pB1101 binary vector, an XbaI site was added by subcloning the PstI/KpnI fragment released from the pT7T3-18U vector into pBluescript II KS+ (Stratagene). The fragment was then excised and cloned in the XbaI site of the pB1101 vector.

The resulting vectors pBnFAE1-GUS and pLaFAE1-GUS in pBI101 were then introduced into A. tumefaciens strain GV3101 by heat-shock, and used to transform Arabidopsis as described above. Transformants were selected on agar-solidified medium containing kanamycin (50 µg/ml). More than 100 transformants were generated for each construct. The activity of the L. annua and B. napus FAE1 promoters was determined by GUS expression assays on the developing seeds and also on non-reproductive plant tissues as controls. Consistent seed-specific GUS expression was obtained for both promoters constructs in independent transgenic lines. In contrast, there was no detectable GUS activity in leaf, stem and silique samples.

References

The following documents are hereby incorporated by reference. Ausubel F M, Brent R, Kingston R E, Moore D D, Seidman J G, Smith J A, Stuhl K, (1995) Current Protocols in Molecular Biology, Vols. 1, 2 and 3.

Benfey, P. N. and Chua, N. H. (1989) Regulated genes in transgenic plants, Science 244, 174–181.

Bevan, M. Shufflebottom, D., Edwards, K., Jefferson, R. and Schuch, W. (1989) Tissue- and cell-specific activity of a phenylalanine ammonia-lyase promoter in trangenic plants. EMBO, J. 8, 1899–1906

Broun, P. and Somerville, C. (1997) Accumulation of ricinoleic, lesquerolic, and densipolic acids in seeds of transgenic Arabidopsis plants that express a fatty acyl hydroxylase cDNA from castor bean, Plant Physiol. 113, 933–942

Chen, Z. L., Pan, N. S., and Beachy, R. N. (1988) A DNA sequence element that confers seed-specific enhancement to a constitutive promoter, EMBO J. 6: 3559–3564.

Clough, S. J. and Bent, A. F. (1998) Floral dip: a simplified method for Agrobacterium-mediated transformation of Arabdiopsis thaliana. Plant J. 16: 735–743.

Devic, M., Albert, S. Delseny, M. and Roscoe, T. J. (1997) Efficient PCR walking on plant genomic DNA, Plant Physiol. Biochem. 35: 331–339.

James, D. W., Jr., Lim, E., Keller, J., Plooy, I., Ralston, E., and Dooner, H. K. (1995) Directed tagging of the Arabidopsis FATTY ACID ELONGATION (FAE1) gene with the maize transpoon Actiatgor, Plant Cell 7: 309–319.

Jefferson, R. A., Kavanaugh, T. and Bevan, M. W. (1987) GUS fusions: β-glucuronidase as a sensitive and versatile gene fusion marker system in higher plants. EMBO J. 6: 3901–3907.

Katavic, V., Haugh, G. W., Reed, D., Martin, M., and Kunst, L. (1994) In planta transformation of Arabidopsis thaliana, Mol. Gen. Genet. 245: 363–370.

Koacz, C. and Schell, J. (1986) The promoter of $T_L$-DNA gene 5 controls the tissue-specific expression of chimeric genes carried by a novel type of Agrobacterium binary vector, *Mol. Gene. Genet.* 204: 383–396.

Kunst, L., Taylor, D. C. and Underhill, E. W. (1992) Fatty acid elongation in developing seeds of *Arabidopsis thaliana, Plant Physiol. Biochem.* 30: 425–434.

Lee D., and Douglas C. J. (1996) Manipulation of plant gene expression using antisense RNA. In: *Plant Biochemistry/Molecular Biology Laboratory Manual,* pp. 423–439. Dashek, W. V., ed., CRC Press, Inc., Boca Raton.

Murphy, D. J., Cummins, L., and Ryan, A. J. (1989) Immunocytochemical and biochemical study of the biosynthesis and mobilisation of the major seed storage proteins of *Brassica napus,* Plant Physiol. Biochem. 27, 647–657.

Stalberg, K., Ellerstoem, M., Ezcurra, I., Ablov, S., and Rask, L. (1996) Disruption of an overlapping e-box-ABRE motif abolished high transcription of the napA storage-protein promoter in transgenic *Brassica napus* seeds. *Planta* 199: 515–519.

Voelker, T. A., Hayes, T. R., Cranmer, A. M., Turner, J. C., and Davies H. M. (1996) Genetic engineering of a quantitative trait: Metabolic and genetic parameters influencing the accumulation of laurate in rapeseed. *Plant J.* 9: 229–241.

What is claimed is:

1. A recombinant nucleic acid molecule comprising a heterologous promoter sequence operably linked to a nucleic acid sequence, wherein the promoter sequence comprises a transcriptional regulatory region capable of directing speed-specific expression in Arabidopsis wherein the transcriptional regulatory region comprises SEQ ID NO: 15 or the complement thereof.

2. The recombinant nucleic acid molecule of claim 1 wherein the nucleic acid sequence encodes an enzyme involved in lipid metabolism.

3. A plant cell comprising a heterologous nucleic acid sequence, wherein the heterologous nucleic acid sequence comprises the recombinant nucleic acid molecule of claim 1.

4. The plant cell of claim 3, wherein the plant cell is of a dicotyledonous plant species.

5. A tangenic plant comprising a heterogenous nucleic acid sequence, wherein the heterologous nucleic acid sequence comprises the recombinant nucleic acid molecule of claim 1.

6. The transgenic plant of claim 5, wherein the plant is of a dicotyledonous plant species.

7. A method of altering the phenotype of a seed comprising:

a) transforming a seed-bearing plant, with a vector comprising the nucleic acid molecule of claim 1; and b) growing the seed-bearing plant to obtain seed wherein the nucleic acid sequence is expressed during embryogenesis under the control of the transcriptional regulatory region to alter the phenotype of the seed.

8. A method of producing a transgenic plant comprising introducing into the plant the recombinant nucleic acid molecule of claim 1.

9. A plant produced by sexual or asexual propagation of the transgenic plant produced according to the method of claim 8, or by propagation of progeny of the transgenic plant, wherein the plant and progeny plant comprises the recombinant nucleic acid molecule.

10. A recombinant vector comprising the nucleic acid molecule according to claim 1.

* * * * *